United States Patent
Valmier

(10) Patent No.: US 10,781,452 B2
(45) Date of Patent: Sep. 22, 2020

(54) FLT3 RECEPTOR ANTAGONISTS FOR THE TREATMENT OR THE PREVENTION OF PAIN DISORDERS

(71) Applicant: Jean Valmier, Montpellier (FR)

(72) Inventor: Jean Valmier, Montpellier (FR)

(73) Assignees: INSTITUT NATIONAL DE LA SANTE ET DE LA RECHERCHE MEDICALE (INSERM), Paris (FR); UNIVERSITE DE MONTPELLIER, Montpellier (FR)

( * ) Notice: Subject to any disclaimer, the term of this patent is extended or adjusted under 35 U.S.C. 154(b) by 0 days.

(21) Appl. No.: 16/129,955

(22) Filed: Sep. 13, 2018

(65) Prior Publication Data

US 2019/0002888 A1 Jan. 3, 2019

Related U.S. Application Data

(60) Continuation-in-part of application No. 15/660,075, filed on Jul. 26, 2017, now Pat. No. 10,106,798, which is a continuation-in-part of application No. 14/793,823, filed on Jul. 8, 2015, now Pat. No. 9,765,339, which is a division of application No. 13/520,598, filed as application No. PCT/EP2011/050103 on Jan. 5, 2011, now Pat. No. 9,109,227.

(30) Foreign Application Priority Data

Jan. 5, 2010 (EP) ..................... 10305013

(51) Int. Cl.
| | | |
|---|---|---|
| A61K 39/00 | (2006.01) |
| A61K 39/395 | (2006.01) |
| C07K 16/28 | (2006.01) |
| C12N 15/113 | (2010.01) |
| G01N 33/50 | (2006.01) |
| A61K 31/553 | (2006.01) |
| A61K 31/404 | (2006.01) |
| C12N 15/115 | (2010.01) |
| A61P 29/00 | (2006.01) |

(52) U.S. Cl.
CPC ........ *C12N 15/1138* (2013.01); *A61K 31/404* (2013.01); *A61K 31/553* (2013.01); *A61P 29/00* (2018.01); *C07K 16/28* (2013.01); *C07K 16/2863* (2013.01); *C12N 15/115* (2013.01); *G01N 33/5032* (2013.01); *G01N 33/5058* (2013.01); *G01N 33/5088* (2013.01); *A61K 2039/505* (2013.01); *C07K 2317/21* (2013.01); *C07K 2317/622* (2013.01); *C07K 2317/76* (2013.01); *C12N 2310/14* (2013.01); *G01N 2333/91205* (2013.01)

(58) Field of Classification Search
None
See application file for complete search history.

(56) References Cited

PUBLICATIONS

MacCallum et al. (1996). J. Mol. Biol. 262:732-745.*
De Pascalis et al. (2002). Journal of Immunology. 169:3076-3084.*
Casset et al. (2003). Biochemical and Biophysical Reseaerch Communications. 307:198-205.*
Chen et al. (1999). J. Mol. biol. 293:865-881.*
Wu et al. (1999). J. Mol. Biol. 294:151-162.*
Rudikoff et al. (1982). PNAS. 79:1979-1983.*

\* cited by examiner

*Primary Examiner* — Joanne Hama
*Assistant Examiner* — Jon M Lockard
(74) *Attorney, Agent, or Firm* — W&C IP

(57) ABSTRACT

The present invention relates to FLT3 receptor antagonists or inhibitors of FLT3 receptor gene expression for the treatment or the prevention of pain disorders.

Figure 1A:
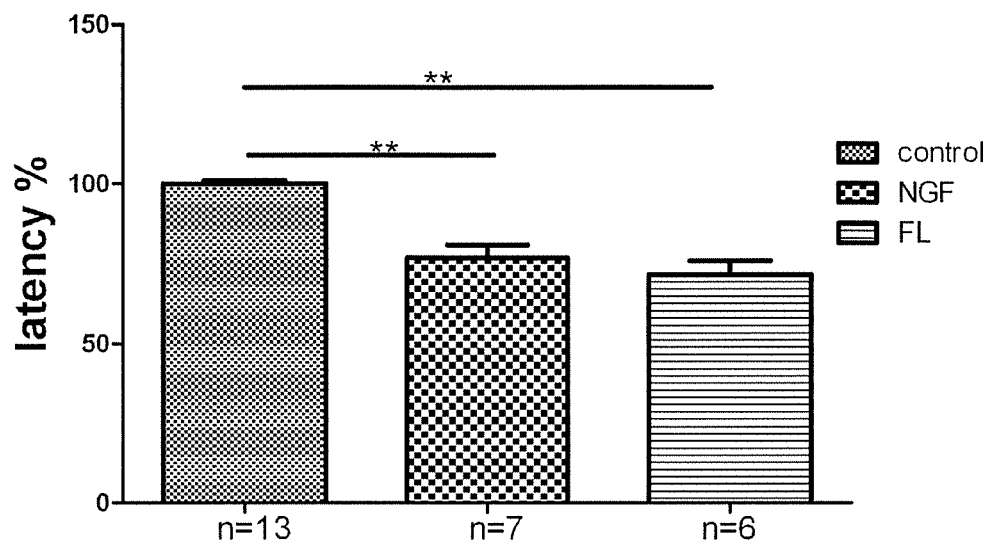

2 Claims, 8 Drawing Sheets
Specification includes a Sequence Listing.

SEQUENCE LISTING

```
<160> NUMBER OF SEQ ID NOS: 12

<210> SEQ ID NO 1
<211> LENGTH: 117
<212> TYPE: PRT
<213> ORGANISM: Artificial Sequence
<220> FEATURE:
<223> OTHER INFORMATION: Synthetic VH domain of A3

<400> SEQUENCE: 1

Glu Val Gln Leu Val Glu Ser Gly Gly Ser Leu Val Lys Pro Gly Gly
1               5                   10                  15

Ser Leu Arg Leu Ser Cys Ala Ala Ser Gly Phe Thr Phe Ser Asn Ser
            20                  25                  30

Tyr Met Asn Trp Val Arg Gln Ala Pro Gly Lys Gly Leu Glu Trp Ile
        35                  40                  45

Ser Asp Ile Ser Gly Ser Ser Arg Asp Ile Asp Tyr Ala Asp Phe Val
    50                  55                  60

Lys Gly Arg Phe Thr Ile Ser Arg Asp Asn Ala Thr Asn Ser Leu Tyr
65                  70                  75                  80

Leu Gln Met Asn Ser Leu Arg Ala Glu Asp Thr Ala Val Tyr Tyr Cys
                85                  90                  95

Val Arg Ser Gly Asn Ser Gly Met Asp Val Trp Gly Arg Gly Thr Leu
            100                 105                 110

Val Thr Val Ser Ser
        115

<210> SEQ ID NO 2
<211> LENGTH: 110
<212> TYPE: PRT
<213> ORGANISM: Artificial Sequence
<220> FEATURE:
<223> OTHER INFORMATION: Synthetic VL region of A3

<400> SEQUENCE: 2

Gln Ser Val Leu Thr Gln Pro Ala Ser Val Ser Gly Ser Pro Gly Gln
1               5                   10                  15

Ser Ile Thr Ile Ser Cys Ala Gly Thr Ser Ser Asp Val Gly Gly Gly
            20                  25                  30
```

```
Tyr Tyr Val Ser Trp Tyr Gln Gln His Pro Gly Lys Ala Pro Lys Leu
             35                  40                  45

Met Ile Tyr Tyr Asp Ser Tyr Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Asn Asn
                 85                  90                  95

Ser Thr Arg Val Phe Gly Gly Gly Thr Lys Leu Glu Ile Lys
            100                 105                 110

<210> SEQ ID NO 3
<211> LENGTH: 5
<212> TYPE: PRT
<213> ORGANISM: Artificial Sequence
<220> FEATURE:
<223> OTHER INFORMATION: Synthetic H-CDR1 of A3

<400> SEQUENCE: 3

Asn Ser Tyr Met Asn
 1               5

<210> SEQ ID NO 4
<211> LENGTH: 17
<212> TYPE: PRT
<213> ORGANISM: Artificial Sequence
<220> FEATURE:
<223> OTHER INFORMATION: Synthetic H-CDR2 of A3

<400> SEQUENCE: 4

Asp Ile Ser Gly Ser Ser Arg Asp Ile Asp Tyr Ala Asp Phe Val Lys
 1               5                   10                  15

Gly

<210> SEQ ID NO 5
<211> LENGTH: 8
<212> TYPE: PRT
<213> ORGANISM: Artificial Sequence
<220> FEATURE:
<223> OTHER INFORMATION: Synthetic H-CDR3 of A3

<400> SEQUENCE: 5

Ser Gly Asn Ser Gly Met Asp Val
 1               5

<210> SEQ ID NO 6
<211> LENGTH: 14
<212> TYPE: PRT
<213> ORGANISM: Artificial Sequence
<220> FEATURE:
<223> OTHER INFORMATION: Synthetic L-CDR1 of A3

<400> SEQUENCE: 6

Ala Gly Thr Ser Ser Asp Val Gly Gly Gly Tyr Tyr Val Ser
 1               5                  10

<210> SEQ ID NO 7
<211> LENGTH: 7
<212> TYPE: PRT
<213> ORGANISM: Artificial Sequence
<220> FEATURE:
<223> OTHER INFORMATION: Synthetic L-CDR2 of A3

<400> SEQUENCE: 7
```

```
Tyr Asp Ser Tyr Arg Pro Ser
1               5

<210> SEQ ID NO 8
<211> LENGTH: 10
<212> TYPE: PRT
<213> ORGANISM: Artificial Sequence
<220> FEATURE:
<223> OTHER INFORMATION: Synthetic L-CDR3 of A3

<400> SEQUENCE: 8

Ser Ser Tyr Thr Asn Asn Ser Thr Arg Val
1               5                   10

<210> SEQ ID NO 9
<211> LENGTH: 19
<212> TYPE: RNA
<213> ORGANISM: Artificial Sequence
<220> FEATURE:
<223> OTHER INFORMATION: Synthetic siRNA targeting FLT3

<400> SEQUENCE: 9
gaaauugacc cguacgaaa                                                    19

<210> SEQ ID NO 10
<211> LENGTH: 19
<212> TYPE: RNA
<213> ORGANISM: Artificial Sequence
<220> FEATURE:
<223> OTHER INFORMATION: Synthetic siRNA targeting FLT3

<400> SEQUENCE: 10
gaaggaacga caccggaua                                                    19

<210> SEQ ID NO 11
<211> LENGTH: 19
<212> TYPE: RNA
<213> ORGANISM: Artificial Sequence
<220> FEATURE:
<223> OTHER INFORMATION: Synthetic siRNA targeting FLT3

<400> SEQUENCE: 11
gauucagagu ggauuuaaa                                                    19

<210> SEQ ID NO 12
<211> LENGTH: 19
<212> TYPE: RNA
<213> ORGANISM: Artificial Sequence
<220> FEATURE:
<223> OTHER INFORMATION: Synthetic siRNA targeting FLT3

<400> SEQUENCE: 12
gcauuccugu cgacgcuaa                                                    19
```

FLT3 RECEPTOR ANTAGONISTS FOR THE TREATMENT OR THE PREVENTION OF PAIN DISORDERS

CROSS-REFERENCE TO RELATED APPLICATIONS

This application is a continuation-in-part (CIP) application of U.S. Ser. No. 15/660,075 filed Jul. 26, 2017, now U.S. Pat. No. 10,106,798, which was a CIP application of U.S. Ser. No. 14/793,823 filed Jul. 8, 2015, now U.S. Pat. No. 9,765,339, which was a divisional application of U.S. Ser. No. 13/520,598 filed Nov. 5, 2012, now U.S. Pat. No. 9,109,227, which itself was a Rule 371 filing of PCT/EP2011/050103 filed Jan. 5, 2011, and that international application claimed priority to European Application 10305013.4 filed Jan. 5, 2010.

FIELD OF THE INVENTION

The present invention relates to FLT3 receptor antagonists or inhibitors of FLT3 receptor gene expression for the treatment or the prevention of pain disorders.

BACKGROUND OF THE INVENTION

Somatic sensations such as warming, cooling, gentle touch and pain are each initiated by activation of sensory neurons. Specific types of sensory neurons, whose cell bodies are located in dorsal root and trigeminal ganglia, subserve different sensory modalities. Specialized sensory neurons called nociceptors are responsible for the transduction of painful thermal and mechanical stimulation of the skin. Knowledge about molecules and ion channels that are necessary for the normal transduction of painful thermal and mechanical stimuli is still incomplete. It has been postulated that thermosensitive ion channels of the TRP family are important for the transduction of noxious heat or cold by nociceptive sensory neurons (Jordt et al., 2003). The most complete evidence exists for the capsaicin activated ion channel TRPV1 that can be activated by thermal stimuli in the noxious range. Mice lacking TRPV1 have altered pain behavior and do not respond to the noxious irritant capsaicin. An important feature of pain is the fact that injury and inflammation leads to heightened sensitivity to stimuli that would normally be only mildly painful. This phenomenon is called hyperalgesia, and the prevention of hyperalgesia is a hallmark of effective analgesia. TRPV1 may become an important analgesic target because this channel is required for the expression of thermal hyperalgesia provoked by inflammation (Caterina et al., 2000; Davis et al., 2000).

Moreover, molecules up-regulated in inflamed tissue such as nerve growth factor (NGF) can sensitize peripheral nociceptors to thermal stimuli. NGF signaling via its receptor tyrosine kinase TrkA constitutes a physiological mediator of inflammatory hyperalgesia. It has been known for many years that the dorsal root ganglion (DRG) neurons that require NGF are all nociceptors. NGF can produce a profound and long lasting thermal and mechanical hyperalgesia in man and animals. NGF can also potentiate TRPV1 mediated and noxious heat activated ionic currents in isolated DRG neurons. Indeed, NGF injected into animals produces thermal hyperalgesia that requires the presence of TRPV1 (Chuang et al., 2001).

Around half of the nociceptors in the adult DRG possess TrkA receptors; the remainder, defined by the expression of c-Ret, downregulate TrkA during early postnatal development. The receptor tyrosine kinase c-Ret mediates signals elicited by the glial-derived neurotophic factor (GDNF) ligand family. The c-Ret receptor and its co-receptors GFRα2 and 3 are present in nociceptive neurons, some of which are heat sensitive and express TRPV1 receptors. Indeed, there is some evidence for a role of the GDNF family ligands neurturin and artemin in regulating noxious heat transduction by sensory neurons (Malin et al., 2006).

In addition to the Trk and c-Ret receptors, sensory neurons are known to express other receptor tyrosine kinases like c-Kit, the receptor for stem cell factor (SCF). Thus, the European patent application No EP 2 068 152 discloses that the central role for SCF and its receptor, c-Kit, in tuning the responsiveness of sensory neurons to natural stimuli and that c-Kit can now be grouped with a small family of receptor tyrosine kinases, including c-Ret and TrkA, that control the transduction properties of sensory neurons. Said patent application claims the use of a c-kit receptor antagonist such as the small molecule drug imatinib for treating or preventing a disorder selected from pain, hyperalgesia and inflammatory pain.

However, no investigation on FLT3 receptor pathway (another tyrosine kinase receptor) has been made until now on pain regulation.

SUMMARY OF THE INVENTION

The present invention relates to a FLT3 receptor antagonist for the treatment or the prevention of pain disorders.

The present invention also relates to an inhibitor of FLT3 receptor gene expression for the treatment or the prevention of pain disorders.

DETAILED DESCRIPTION OF THE INVENTION

Definitions

Throughout the specification, several terms are employed and are defined in the following paragraphs.

The terms "FLT3" or "FLT3 receptor" (fms-related tyrosine kinase 3), also known as the CD135, Ly72, Flk-2, Flt-3 or B230315G04, are used interchangeably and have their general meaning in the art. The FLT3 receptor can be from any source, but typically is a mammalian (e.g., human and non-human primate) FLT3 receptor, particularly a human FLT3 receptor.

The terms "FL" or "FLT3-Ligand" are used interchangeably and have their general meaning in the art. They refer to the cytokine which is a natural ligand of the FLT3 receptor. FL can be from any source, but typically is a mammalian (e.g., human and non-human primate) FL, particularly a human FL.

An "inhibitor of gene expression" refers to a natural or synthetic compound that has a biological effect to inhibit or significantly reduce the expression of a gene. Consequently an "inhibitor of FLT3 receptor gene expression" refers to a natural or synthetic compound that has a biological effect to inhibit or significantly reduce the expression of the gene encoding for the FLT3 receptor.

By "receptor antagonist" is meant a natural or synthetic compound that has a biological effect opposite to that of a receptor agonist. The term is used indifferently to denote a "true" antagonist and an inverse agonist of a receptor. A "true" receptor antagonist is a compound which binds the receptor and blocks the biological activation of the receptor, and thereby the action of the receptor agonist, for example, by competing with the agonist for said receptor. An inverse agonist is a compound which binds to the same receptor as the agonist but exerts the opposite effect. Inverse agonists have the ability to decrease the constitutive level of receptor activation in the absence of an agonist.

The terms "FLT3 receptor antagonist" includes any entity that, upon administration to a patient, results in inhibition or down-regulation of a biological activity associated with activation of the FLT3 receptor by FL in the patient, including any of the downstream biological effects otherwise resulting from the binding to FLT3 receptor with FL. Such FLT3 receptor antagonists include any agent that can block FLT3 receptor activation or any of the downstream biological effects of FLT3 receptor activation. For example, such a FLT3 receptor antagonist (e.g. a small organic molecule, an antibody directed against FLT3) can act by occupying the ligand binding site or a portion thereof of the FLT3 receptor, thereby making FLT3 receptor inaccessible to its natural ligand, FL, so that its normal biological activity is prevented or reduced. The term FLT3 receptor antagonist includes also any agent able to interact with the natural ligand of FLT3, namely FL. Said agent may be an antibody directed against FL which can block the interaction between FL and FLT3 or which can block the activity of FL ("neutralizing antibody").

The term "blocking the interaction", "inhibiting the interaction" or "inhibitor of the interaction" are used herein to mean preventing or reducing the direct or indirect association of one or more molecules, peptides, proteins, enzymes or receptors; or preventing or reducing the normal activity of one or more molecules, peptides, proteins, enzymes, or receptors. The term "inhibitor of the interaction between FLT3 and FL" is a molecule which can prevent the interaction between FLT3 and FL by competition or by fixing to one of the molecule.

In the context of the present invention, when FLT3 receptor antagonists are small organic molecules, said antagonists are preferably selective for the FLT3 receptor as compared with the other tyrosine kinase receptors, such as c-Kit receptor. By "selective" it is meant that the affinity of the antagonist for the FLT3 receptor is at least 10-fold, preferably 25-fold, more preferably 100-fold, still preferably 150-fold higher than the affinity for the other tyrosine kinase receptors (c-Kit receptor). Selectivity of a FLT3 receptor antagonists may be assayed for instance by carrying out biochemical kinase binding assays such as KinomeScan kinase binding assays as described in Fabian et al. 2005 and Karaman et al. 2008. For the FLT3 assay, a kinase construct that spanned the catalytic domain only (amino acids 592 to 969 in NP_004110.2) may be used. This construct does not include the juxtamembrane domain and is designed to measure the intrinsic binding affinity of the open FLT3 active site for inhibitors as previously described in Zarrinkar et al. 2009.

The affinity of an antagonist for FLT3 receptor may be quantified by measuring the activity of FLT3 receptor in the presence a range of concentrations of said antagonist in order to establish a dose-response curve. From that dose response curve, an $IC_{50}$ value may be deduced which represents the concentration of antagonist necessary to inhibit 50% of the response to an agonist in defined concentration. The $IC_{50}$ value may be readily determined by the one skilled in the art by fitting the dose-response plots with a dose-response equation as described by De Lean et al. 1979. $IC_{50}$ values can be converted into affinity constant (Ki) using the assumptions of Cheng and Prusoff (1973).

The term "small organic molecule" refers to a molecule of a size comparable to those organic molecules generally used in pharmaceuticals. The term excludes biological macromolecules (e. g., proteins, nucleic acids, etc.). Preferred small organic molecules range in size up to about 5000 Da, more preferably up to 2000 Da, and most preferably up to about 1000 Da.

The term "antibody" as used herein refers to immunoglobulin molecules and immunologically active portions of immunoglobulin molecules, i.e., molecules that contain an antigen binding site that immunospecifically binds an antigen. As such, the term antibody encompasses not only whole antibody molecules, but also antibody fragments as well as variants (including derivatives) of antibodies and antibody fragments. In natural antibodies, two heavy chains are linked to each other by disulphide bonds and each heavy chain is linked to a light chain by a disulphide bond. There are two types of light chain, lambda (l) and kappa (k). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CHI, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, transplacental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions (FR) can participate to the antibody binding site or influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, typically includes six CDRs, comprising the CDR set from each of a heavy and a light chain V region. Framework Regions (FRs) refer to amino acid sequences interposed between CDRs. The residues in antibody variable domains are conventionally numbered according to a system devised by Kabat et al. This system is set forth in Kabat et al., 1987, in Sequences of Proteins of Immunological Interest, US Department of Health and Human Services, NIH, USA (hereafter "Kabat et al."). This numbering system is used in the present specification. The Kabat residue designations do not always correspond directly with the linear numbering of the amino acid residues in SEQ ID sequences. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence.

Encompassed herein are antibodies with amino acid sequences that are at least about 50% identical to the sequences disclosed herein, e.g. at least about 50, 55, 60, 65, 70, 75, 80, 85, 90 or 95% identical. The sequences may be, for example, 90, 91, 92, 93, 94, 95, 96, 97, 98, or 99% identical. Amino acid sequence identity is determined using a suitable sequence alignment algorithm and default parameters, such as BLAST P (Karlin and Altschul, Proc. Natl Acad. Sci. USA 87(6):2264-2268 (1990)).

As used herein, the term "subject" denotes a mammal, such as a rodent, a feline, a canine, and a primate. Preferably, a subject according to the invention is a human.

The term "pain disorders" refers to disorder selected in the group consisting of acute pain, chronic pain, neuropathic pain, inflammatory pain, low back pain, post-operative pain, cancer pain, vascular headache such as migraine, fibromyalgia, hyperalgesia such as mechanical and thermal hyperalgesia, allodynia such as thermal and mechanical allodynia, peripheral sensitization of pain mechanisms and central sensitization of pain mechanisms.

In its broadest meaning, the term "treating" or "treatment" refers to reversing, alleviating, inhibiting the progress of, or preventing the disorder or condition to which such term applies, or one or more symptoms of such disorder or condition.

In particular, "prevention" of pain may refer to the administration of the compounds of the present invention prevent the symptoms of pain.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

Therapeutic Methods and Uses

The present invention provides methods and compositions (such as pharmaceutical compositions) for treating or preventing pain disorders.

According to a first aspect, the invention relates to a FLT3 receptor antagonist for treating or preventing pain disorders.

In one embodiment, the FLT3 receptor antagonist may be a low molecular weight antagonist, e.g. a small organic molecule.

Exemplary FLT3 receptor antagonists that are contemplated by the invention include but are not limited to those described in Sternberg et al. 2004 and in International Patent Application Nos WO 2002032861, WO 2002092599, WO 2003035009, WO 2003024931, WO 2003037347, WO 2003057690, WO 2003099771, WO 2004005281, WO 2004016597, WO 2004018419, WO 2004039782, WO 2004043389, WO 2004046120, WO 2004058749, WO 2004058749, WO 2003024969, WO 2006/138155, WO 2007/048088 and WO 2009/095399 which are incorporated herein by reference.

More particularly, FLT3 receptor antagonists may consist in FLT3 kinase inhibitors. Exemplary of FLT3 kinase inhibitors that are contemplated include AG1295 and AG1296; Lestaurtinib (also known as CEP-701, formerly KT-5555, Kyowa Hakko, licensed to Cephalon); CEP-5214 and CEP-7055 (Cephalon); CHIR-258 (Chiron Corp.); GTP 14564 (Merk Biosciences UK). Midostaurin (also known as PKC 412 Novartis AG); MLN-608 (Millennium USA); MLN-518 (formerly CT53518, COR Therapeutics Inc., licensed to Millennium Pharmaceuticals Inc.); MLN-608 (Millennium Pharmaceuticals Inc.); SU-11248 (Pfizer USA); SU-11657 (Pfizer USA); SU-5416 and SU-5614; THRX-165724 (Theravance Inc.); AMI-10706 (Theravance Inc.); VX-528 and VX-680 (Vertex Pharmaceuticals USA, licensed to Novartis (Switzerland), Merck & Co USA); and XL 999 (Exelixis USA).

In a preferred embodiment, the FLT3 receptor antagonist is a selective FLT3 receptor antagonist.

Exemplary selective FLT3 receptor antagonists that are contemplated by the invention include but are not limited to those described in Zarrinkar et al. 2009 and in International Patent Applications No WO 2007/109120 and WO 2009/061446 which are incorporated herein by reference. Accordingly, in a most preferred embodiment, the selective FLT3 receptor antagonist is the compound known as AC220 or N-(5-tert-butyl-isoxazol-3-yl)-N'-{4-[7-(2-morpholin-4-yl-ethoxy)imidazo[2,1-b] [1,3]benzothiazol-2-yl]phenyl}urea dihydrochloride. Said AC220 compound may be made by methods known in the art, for example, as described in the international patent application WO 2007/109120.

In another embodiment, the FLT3 receptor antagonist is an inhibitor of the interaction between FLT3 and FL.

The compounds that inhibit the interaction between FLT3 and FL encompass those compounds that bind either to the FLT3 or to FL, provided that the binding of the said compounds of interest then prevent the interaction between FLT3 and FL. Accordingly, said compounds may be selected from the group consisting of peptides, peptidomimetics, small organic molecules, antibodies, aptamers or nucleic acids.

In another embodiment, the FLT3 receptor antagonist may consist in an antibody (the term including antibody fragment) that can block FLT3 receptor activation. In particular, the FLT3 receptor antagonist may consist in an antibody directed against the FLT3 receptor or FL, in such a way that said antibody impairs the binding of a FL to FLT3.

In a particular embodiment, the FLT3 receptor antagonist may be an anti-FLT3 neutralizing antibody such as IMC-EB10 described in Li et al., 2004 and in US patent application No US 2009/0297529 which are incorporated herein by reference.

In another particular embodiment, the FLT3 receptor antagonist may be an anti-FL neutralizing antibody.

Antibodies directed against the FLT3 receptor or FL can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred. Monoclonal antibodies against FLT3 receptor or FL can be prepared and isolated using any technique that provides for the production of antibody molecules by continuous cell lines in culture. Techniques for production and isolation include but are not limited to the hybridoma technique originally described by Kohler and Milstein (1975); the human B-cell hybridoma technique (Cote et al., 1983); and the EBV-hybridoma technique (Cole et al. 1985). Alternatively, techniques described for the production of single chain antibodies (see, e.g., U.S. Pat. No. 4,946,778) can be adapted to produce anti-FLT3, or anti-FL single chain antibodies. FLT3 receptor antagonists useful in practicing the present invention also include anti-FLT3, or anti-FL antibody fragments including but not limited to F(ab')₂ fragments, which can be generated by pepsin digestion of an intact antibody molecule, and Fab fragments, which can be generated by reducing the disulfide bridges of the F(ab')₂ fragments. Alternatively, Fab and/or scFv expression libraries can be constructed to allow rapid identification of fragments having the desired specificity to FLT3 receptor.

Humanized anti-FLT3 receptor or anti-FL antibodies and antibody fragments therefrom can also be prepared according to known techniques. "Humanized antibodies" are forms of non-human (e.g., rodent) chimeric antibodies that contain minimal sequence derived from non-human immunoglobulin. For the most part, humanized antibodies are human immunoglobulins (recipient antibody) in which residues from a hypervariable region (CDRs) of the recipient are replaced by residues from a hypervariable region of a non-human species (donor antibody) such as mouse, rat, rabbit or nonhuman primate having the desired specificity, affinity and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. Methods for making humanized antibodies are described, for example, by Winter (U.S. Pat. No. 5,225,539) and Boss (Celltech, U.S. Pat. No. 4,816, 397).

Then after raising antibodies directed against the FLT3 receptor or FL as above described, the skilled man in the art can easily select those blocking FLT3 receptor activation.

In another embodiment the FLT3 receptor antagonist is an aptamer directed against FLT3 or FL. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S.D., 1999. Peptide aptamers consists of a conformationally constrained antibody variable region displayed by a platform protein, such as E. coli Thioredoxin A that are selected from combinatorial libraries by two hybrid methods (Colas et al., 1996).

Then after raising aptamers directed against the FLT3 receptor or FL as above described, the skilled man in the art can easily select those blocking FLT3 receptor activation.

Another aspect of the invention relates to an inhibitor of FLT3 receptor gene expression for treating or preventing pain disorders.

Inhibitors of FLT3 receptor gene expression for use in the present invention may be based on anti-sense oligonucleotide constructs. Anti-sense oligonucleotides, including antisense RNA molecules and anti-sense DNA molecules, would act to directly block the translation of FLT3 receptor mRNA by binding thereto and thus preventing protein translation or increasing mRNA degradation, thus decreasing the level of FLT3 receptors, and thus activity, in a cell. For example, antisense oligonucleotides of at least about 15 bases and complementary to unique regions of the mRNA transcript sequence encoding FLT3 receptor can be synthesized, e.g., by conventional phosphodiester techniques and administered by e.g., intravenous injection or infusion. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732).

Small inhibitory RNAs (siRNAs) can also function as inhibitors of FLT3 receptor gene expression for use in the present invention. FLT3 receptor gene expression can be reduced by contacting a subject or cell with a small double stranded RNA (dsRNA), or a vector or construct causing the production of a small double stranded RNA, such that FLT3 receptor gene expression is specifically inhibited (i.e. RNA interference or RNAi). Methods for selecting an appropriate dsRNA or dsRNA-encoding vector are well known in the art for genes whose sequence is known (e.g. see Tuschl, T. et al. (1999); Elbashir, S. M. et al. (2001); Hannon, G J. (2002); McManus, MT. et al. (2002); Brummelkamp, T R. et al. (2002); U.S. Pat. Nos. 6,573,099 and 6,506,559; and International Patent Publication Nos. WO 01/36646, WO 99/32619, and WO 01/68836).

In one embodiment, the sequence of the siRNA targeting FLT3 is represented by SEQ ID NO: 9.

In another embodiment, the sequence of the siRNA targeting FLT3 is represented by SEQ ID NO: 10.

In another embodiment, the sequence of the siRNA targeting FLT3 is represented by SEQ ID NO: 11.

In still another embodiment, the sequence of the siRNA targeting FLT3 is represented by SEQ ID NO: 12.

In a preferred embodiment, a pool of siRNAs targeting FLT3 may be used. Such pool may comprise at least 2 siRNAs selected from SEQ ID NO: 9, SEQ ID NO: 10, SEQ ID NO: 11 and SEQ ID NO: 12.

It must be further noted that such a pool of siRNAs targeting FLT3 may be used as inhibitors of murine and human FLT3 receptor gene expression.

Ribozymes can also function as inhibitors of FLT3 receptor gene expression for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of FLT3 receptor mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Both antisense oligonucleotides and ribozymes useful as inhibitors of FLT3 receptor gene expression can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. arious modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Antisense oligonucleotides siRNAs and ribozymes of the invention may be delivered in vivo alone or in association with a vector. In its broadest sense, a "vector" is any vehicle capable of facilitating the transfer of the antisense oligonucleotide siRNA or ribozyme nucleic acid to the cells and preferably cells expressing FLT3 receptor. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the the antisense oligonucleotide siRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rouse sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Preferred viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, 1990 and in Murry, 1991).

Preferred viruses for certain applications are the adeno-viruses and adeno-associated viruses, which are double-stranded DNA viruses that have already been approved for human use in gene therapy. The adeno-associated virus can be engineered to be replication deficient and is capable of infecting a wide range of cell types and species. It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g. Sambrook et al., 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

Another aspect of the invention relates to a method for treating or preventing pain disorders comprising administering a subject in need thereof with a FLT3 receptor antagonist or an inhibitor of FLT3 receptor gene expression.

FLT3 receptor antagonists or inhibitors of FLT3 receptor gene expression may be administered in the form of a pharmaceutical composition, as defined below. Preferably, said antagonist or inhibitor is administered in a therapeutically effective amount.

By a "therapeutically effective amount" is meant a sufficient amount of the FLT3 receptor antagonist or inhibitor of FLT3 receptor gene expression to treat or to prevent pain e.g. chronic pain at a reasonable benefit/risk ratio applicable to any medical treatment.

It will be understood that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidential with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the patient to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

Screening Methods

A further aspect of the invention relates a method for screening an FLT3 receptor antagonist for the treatment or prevention of pain disorders.

For example, the screening method may measure the binding of a candidate compound to FLT3, or to cells or membranes bearing FLT3, or a fusion protein thereof by means of a label directly or indirectly associated with the candidate compound.

Alternatively, a screening method may involve measuring or, qualitatively or quantitatively, detecting ability of said candidate compound to modulate the intracellular $[Ca^{2+}]$, and efficiently treats and protects against pain disorders.

In a particular embodiment, the screening method of the invention comprises the steps consisting of:
 a) providing a plurality of cells expressing FLT3 on their surface;
 b) incubating said cells with a candidate compound;
 c) determining whether said candidate compound binds to and inhibits FLT3; and
 d) selecting the candidate compound that binds to and inhibits FLT3.

In a particular embodiment, the screening method of the invention may further comprising a step consisting of administering the candidate compound selected at step d) to an animal model of pains disorders to validate the therapeutic and/or protective effects of said candidate compound on pains disorders.

In one preferred embodiment, the FLT3 receptor antagonist is a selective FLT3 receptor antagonist.

In general, such screening methods involve providing appropriate cells which express FLT3 on their surface. In particular, a nucleic acid encoding FLT3 may be employed to transfect cells to thereby express the receptor of the invention. Such a transfection may be accomplished by methods well known in the art.

In a particular embodiment, said cells may be selected from the group consisting of the mammal cells reported yet to express FLT3 (e.g. dorsal root ganglia (DRG) neurones).

The screening method of the invention may be employed for determining an antagonist by contacting such cells with compounds to be screened and determining whether such compound inhibits FLT3.

In another particular embodiment, the screening method of the invention comprises the steps consisting:

a) determining the ability of a candidate compound to inhibit the interaction between a FLT3 polypeptide and a FL polypeptide and
 b) selecting positively the candidate compound that inhibits said interaction.

At step a), any method suitable for the screening of protein-protein interactions is suitable.

Whatever the embodiment of step a) of the screening method, the complete FLT3 protein and the complete FL protein may be used as the binding partners. It should further be noted that fragments of FLT3 protein and FL protein that include the site of interaction may be used as the binding partners.

The term "polypeptide" means herein a polymer of amino acids having no specific length. Thus, peptides, oligopeptides and proteins are included in the definition of "polypeptide" and these terms are used interchangeably throughout the specification, as well as in the claims. The term "polypeptide" does not exclude post-translational modifications that include but are not limited to phosphorylation, acetylation, glycosylation and the like. Also encompassed by this definition of "polypeptide" are homologs thereof.

Accordingly, the term "FLT3 polypeptide" refers to the FLT3 protein or a fragment thereof that comprises the site of interaction with FL protein. In the same manner, the term "FL polypeptide" refers to the FL protein or a fragment thereof that comprises the site of interaction with FLT3 protein.

The compounds that inhibit the interaction between FLT3 and FL encompass those compounds that bind either to the FLT3 or to FL, provided that the binding of the said compounds of interest then prevent the interaction between FLT3 and FL.

Polypeptides of the invention may be produced by any technique known per se in the art, such as without limitation, any chemical, biological, genetic or enzymatic technique, either alone or in combination(s).

Knowing the amino acid sequence of the desired sequence, one skilled in the art can readily produce said polypeptides, by standard techniques for production of polypeptides. For instance, they can be synthesized using well-known solid phase method, preferably using a commercially available peptide synthesis apparatus (such as that made by Applied Biosystems, Foster City, Calif.) and following the manufacturer's instructions.

Alternatively, the polypeptides of the invention can be synthesized by recombinant DNA techniques as is now well-known in the art. For example, these fragments can be obtained as DNA expression products after incorporation of DNA sequences encoding the desired (poly)peptide into expression vectors and introduction of such vectors into suitable eukaryotic or prokaryotic hosts that will express the desired polypeptide, from which they can be later isolated using well-known techniques.

Labelled Polypeptides

In one embodiment, the FLT3 polypeptide or the FL polypeptide of the invention is labelled with a detectable molecule for the screening purposes.

Accordingly, said detectable molecule may consist of any compound or substance that is detectable by spectroscopic, photochemical, biochemical, immunochemical or chemical means. For example, useful detectable molecules include radioactive substance (including those comprising $32P$, $25S$, $3H$, or $125I$), fluorescent dyes (including 5-bromodesosyrudin, fluorescein, acetylaminofluorene or digoxigenin), fluorescent proteins (including GFPs and YFPs), or detectable proteins or peptides (including biotin, polyhistidine tails or other antigen tags like the HA antigen, the FLAG antigen, the c-myc antigen and the DNP antigen).

According to the invention, the detectable molecule is located at, or bound to, an amino acid residue located outside the said amino acid sequence of interest, in order to minimise or prevent any artefact for the binding between said polypeptides or between the candidate compound and or any of said polypeptides.

Fluorescence Assays

In another embodiment of the screening method of the invention, the FLT3 polypeptide and the FL polypeptide as above defined are labelled with a fluorescent molecule or substrate. Therefore, the potential inhibition effect of the candidate compound to be tested on the binding between the FLT3 polypeptide and the FL polypeptide as above defined is determined by fluorescence quantification.

For example, the FLT3 polypeptide and the FL polypeptide as above defined may be fused with auto-fluorescent polypeptides, as GFP or YFPs as above described. The FLT3 polypeptide and the FL polypeptide as above defined may also be labelled with fluorescent molecules that are suitable for performing fluorescence detection and/or quantification for the binding between said polypeptides using fluorescence energy transfer (FRET) assay. The FLT3 polypeptide and the FL polypeptide as above defined may be directly labelled with fluorescent molecules, by covalent chemical linkage with the fluorescent molecule as GFP or YFP. The FLT3 polypeptide and the FL polypeptide as above defined may also be indirectly labelled with fluorescent molecules, for example, by non-covalent linkage between said polypeptides and said fluorescent molecule. Actually, said FLT3 polypeptide and FL polypeptide as above defined may be fused with a receptor or ligand and said fluorescent molecule may be fused with the corresponding ligand or receptor, so that the fluorescent molecule can non-covalently bind to said FLT3 polypeptide and FL polypeptide. A suitable receptor/ligand couple may be the biotin/streptavidin paired member or may be selected among an antigen/antibody paired member. For example, a polypeptide according to the invention may be fused to a poly-histidine tail and the fluorescent molecule may be fused with an antibody directed against the poly-histidine tail.

As already specified, step a) of the screening method of the invention encompasses determination of the ability of the candidate compound to inhibit the interaction between the FLT3 polypeptide and the FL polypeptide as above defined by fluorescence assays using FRET. Thus, in a particular embodiment, the FLT3 polypeptide as above defined is labelled with a first fluorophore substance and the FL polypeptide is labelled with a second fluorophore substance. The first fluorophore substance may have a wavelength value that is substantially equal to the excitation wavelength value of the second fluorophore, whereby the bind of said first and second polypeptides is detected by measuring the fluorescence signal intensity emitted at the emission wavelength of the second fluorophore substance. Alternatively, the second fluorophore substance may also have an emission wavelength value of the first fluorophore, whereby the binding of said and second polypeptides is detected by measuring the fluorescence signal intensity emitted at the wavelength of the first fluorophore substance.

The fluorophores used may be of various suitable kinds, such as the well-known lanthanide chelates. These chelates have been described as having chemical stability, long-lived fluorescence (greater than 0.1 ms lifetime) after bioconjugation and significant energy-transfer in specificity bioaffinity assay.

In a preferred embodiment, the fluorescence assay performed at step a) of the screening method consists of a Homogeneous Time Resolved Fluorescence (HTRF) assay, such as described in document WO 00/01663 or U.S. Pat. No. 6,740,756, the entire content of both documents being herein incorporated by reference. HTRF is a TR-FRET based technology that uses the principles of both TRF (time-resolved fluorescence) and FRET. More specifically, the one skilled in the art may use a HTRF assay based on the time-resolved amplified cryptate emission (TRACE) technology as described in Leblanc et al., 2002. The HTRF donor fluorophore is Europium Cryptate, which has the long-lived emissions of lanthanides coupled with the stability of cryptate encapsulation. XL665, a modified allophycocyanin purified from red algae, is the HTRF primary acceptor fluorophore. When these two fluorophores are brought together by a biomolecular interaction, a portion of the energy captured by the Cryptate during excitation is released through fluorescence emission at 620 nm, while the remaining energy is transferred to XL665. This energy is then released by XL665 as specific fluorescence at 665 nm. Light at 665 nm is emitted only through FRET with Europium. Because Europium Cryptate is always present in the assay, light at 620 nm is detected even when the biomolecular interaction does not bring XL665 within close proximity.

Therefore in one embodiment, step a) of the screening method may therefore comprise the steps consisting of:
  (1) bringing into contact a pre-assay sample comprising:
  a FLT3 polypeptide fused to a first antigen,
  a FL polypeptide fused to a second antigen
  a candidate compound to be tested
  (2) adding to the said pre assay sample of step (2):
  at least one antibody labelled with a European Cryptate which is specifically directed against the first said antigen
  at least one antibody labelled with XL665 directed against the second said antigen
  (3) illuminating the assay sample of step (2) at the excitation wavelength of the said European Cryptate
  (4) detecting and/or quantifying the fluorescence signal emitted at the XL665 emission wavelength
  (5) comparing the fluorescence signal obtained at step (4) to the fluorescence obtained wherein pre assay sample of step (1) is prepared in the absence of the candidate compound to be tested.

If at step (5) as above described, the intensity value of the fluorescence signal is different (lower or higher) than the intensity value of the fluorescence signal found when pre assay sample of step (1) is prepared in the absence of the candidate compound to be tested, then the candidate compound may be positively selected at step b) of the screening method.

Antibodies labelled with a European Cryptate or labelled with XL665 can be directed against different antigens of interest including GST, poly-histidine tail, DNP, c-myx, HA antigen and FLAG which include. Such antibodies encompass those which are commercially available from CisBio (Bedfors, Mass., USA), and notably those referred to as 61GSTKLA or 61HISKLB respectively.

According to one embodiment of the invention, the candidate compounds may be selected from a library of compounds previously synthesised, or a library of compounds for which the structure is determined in a database, or from a library of compounds that have been synthesised de novo or natural compounds.

The candidate compound may be selected from the group of (a) proteins or peptides, (b) nucleic acids and (c) organic or chemical compounds (natural or not).

Such the method may be used to screen FLT3 receptor antagonist according to the invention.

Pharmaceutical Compositions

The FLT3 receptor antagonist or inhibitor of FLT3 receptor gene expression may be combined with pharmaceutically acceptable excipients, and optionally sustained-release matrices, such as biodegradable polymers, to form therapeutic compositions.

In the pharmaceutical compositions of the present invention, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The FLT3 receptor antagonist or inhibitor of FLT3 receptor gene expression of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active polypeptides in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

The FLT3 receptor antagonist or inhibitor of FLT3 receptor gene expression of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds of the invention formulated for parenteral administration, such as intravenous or intramuscular injection, other pharmaceutically acceptable forms include, e.g. tablets or other solids for oral administration; liposomal formulations; time release capsules; and any other form currently used.

The FLT3 receptor antagonist or inhibitor of FLT3 receptor gene expression of the invention may also be used in combination with other therapeutically active agents, for instance, inhibitors of receptor tyrosine kinase (RTK) class III or RTK class VII inhibitors.

RTK class III (Platelet-derived Growth factor (PDGF) receptor family) is a class of receptor tyrosine kinases including c-KIT and c-fms.

RTK class VII (Tropomyosin-receptor-kinase (Trk) receptor family) is a class of receptor tyrosine kinases including TrkA, TrkB and TrkC.

The foregoing therapeutically active agents are listed by way of example and are not meant to be limiting. Other therapeutically active agents which are currently available or that may be developed in the future are equally applicable.

Accordingly, pharmaceutical compositions of the invention as described above may further comprise one or more therapeutically active agents selected in the group consisting of class III RTK inhibitors or class VII RTK inhibitors.

Moreover, if they are contained in different pharmaceutical compositions, said compositions may be administered to the patient at the same time or successively. Thus, the present invention also relates to a kit for the prevention or treatment of an inflammatory disease comprising a first pharmaceutical composition comprising a polypeptide or a compound according to the invention and a second pharmaceutical composition comprising one or more therapeutically active agents selected from the group consisting of class III RTK inhibitors or class VII RTK inhibitors.

The invention will be further illustrated by the following figures and examples. However, these examples and figures should not be interpreted in any way as limiting the scope of the present invention.

FIGURES

Figure 1B:
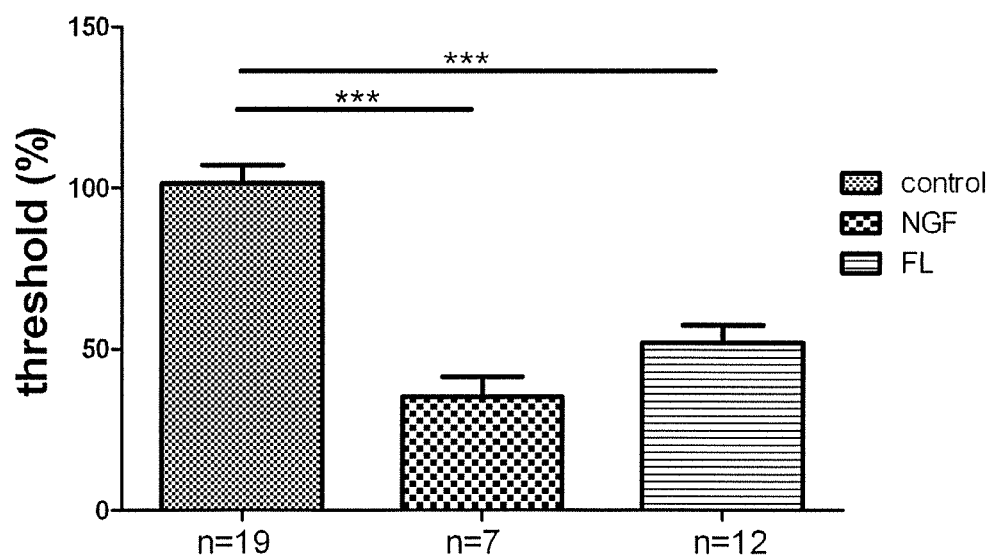

FIG. 1A-B: FL induces thermal and mechanical hyperalgesia in vivo: FL or NGF (as positive control) was injected into mice hindpaws. (A) Behavioral analysis of the effect of FL injection on paw withdrawal latencies in response to radiant heat. $P<0.01$. (B) Behavioral analysis of the effect of FL injection on the foot withdrawal response to von Frey hair filaments. *$P<0.001$.

Figure 2A:
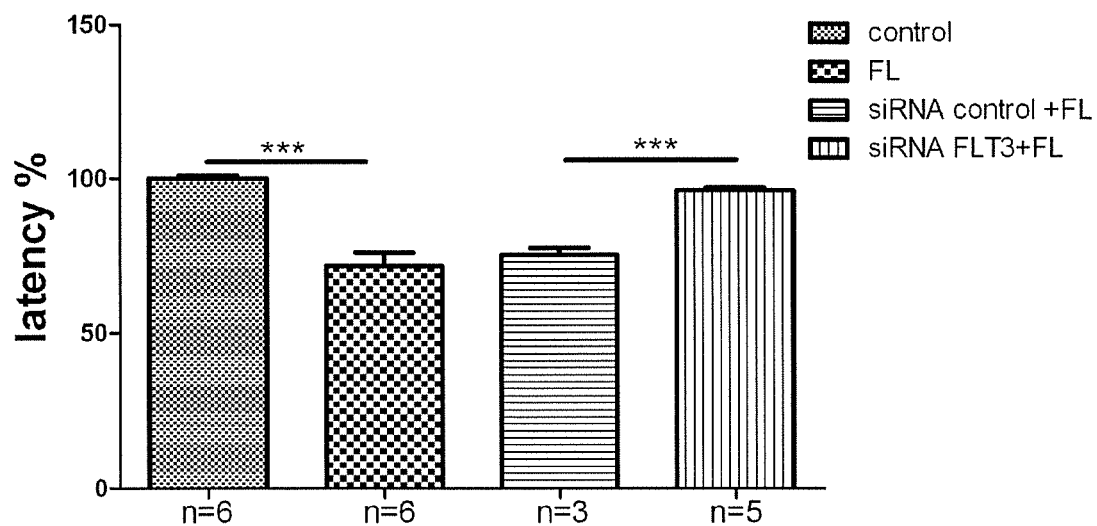
Figure 2B:
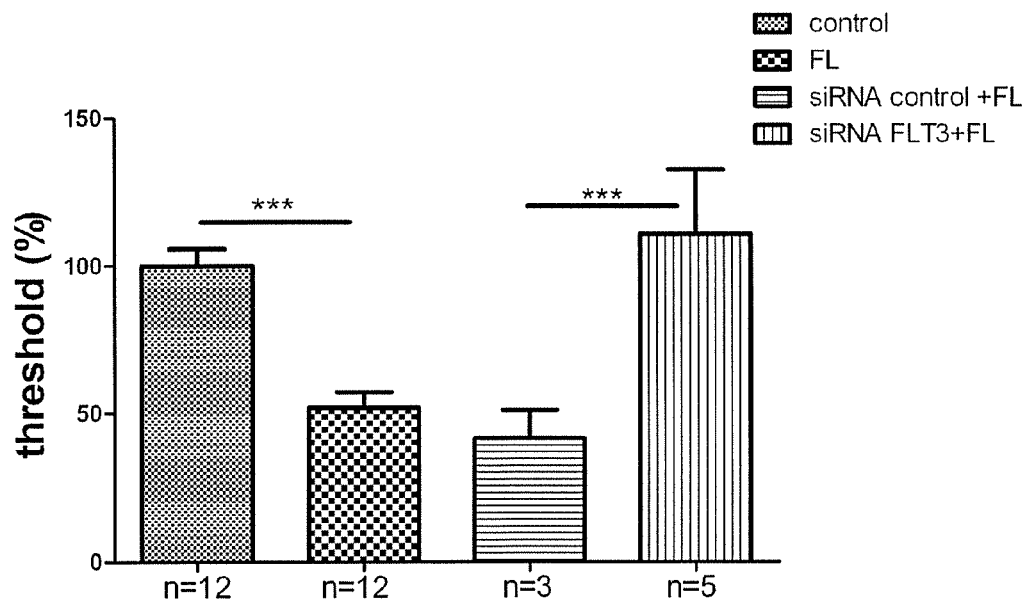

FIG. 2A-B: siRNA against FLT3 inhibits FL-induced thermal and mechanical hyperalgesia in vivo: (A) Behavioral analysis of the effect of intrathecally-delivered FLT3 siRNA on radiant heat induced paw withdrawal latencies after FL injection. *$P<0.001$. (B) Behavioral analysis of the effect of intrathecally-delivered FLT3 siRNA on paw withdrawal latencies in response to von Frey hair filaments after FL injection. *$P<0.001$.

Figure 3A:
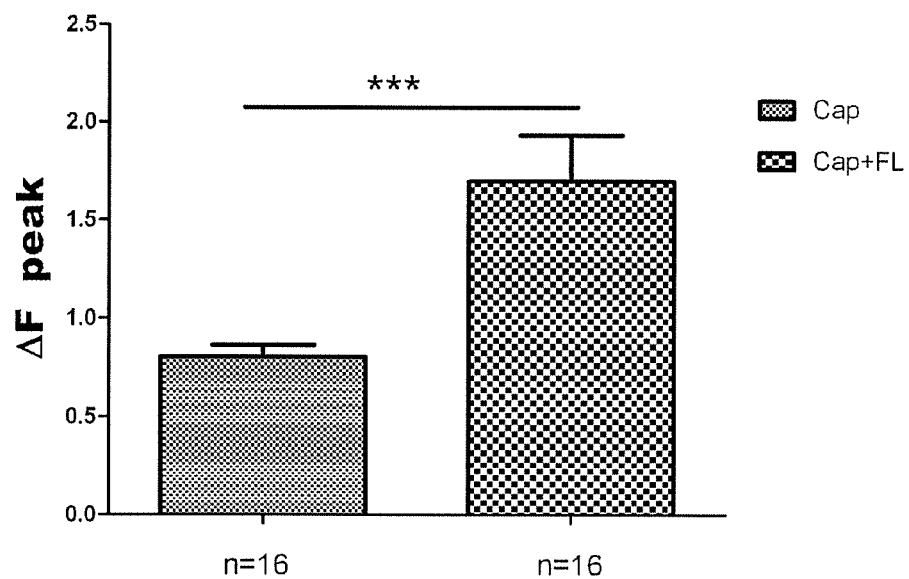
Figure 3B:
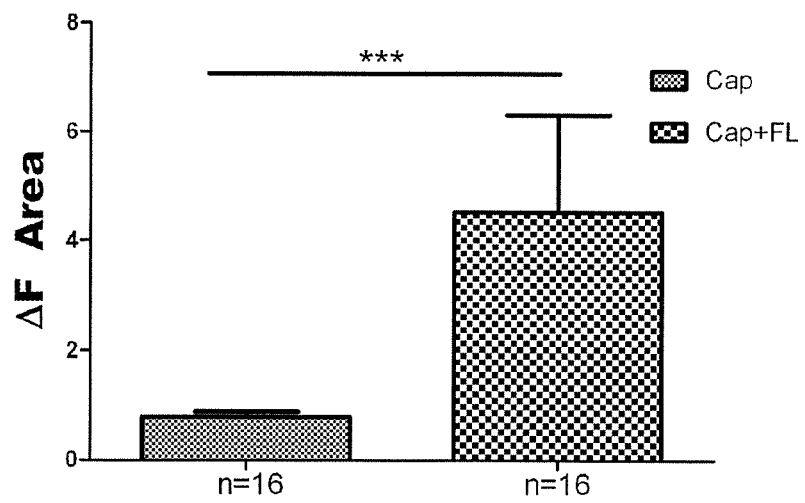

FIG. 3A-B: FL potentiates capsaicin activation of TRPV1 receptors in primary sensory neurons in vitro: (A) ΔFpeak of capsaicin responses before and after FL application in adult DRG neurons. *$P<0.001$. (B) ΔFarea of capsaicin responses before and after FL application in adult DRG neurons. *$P<0.001$.

Figure 4A:
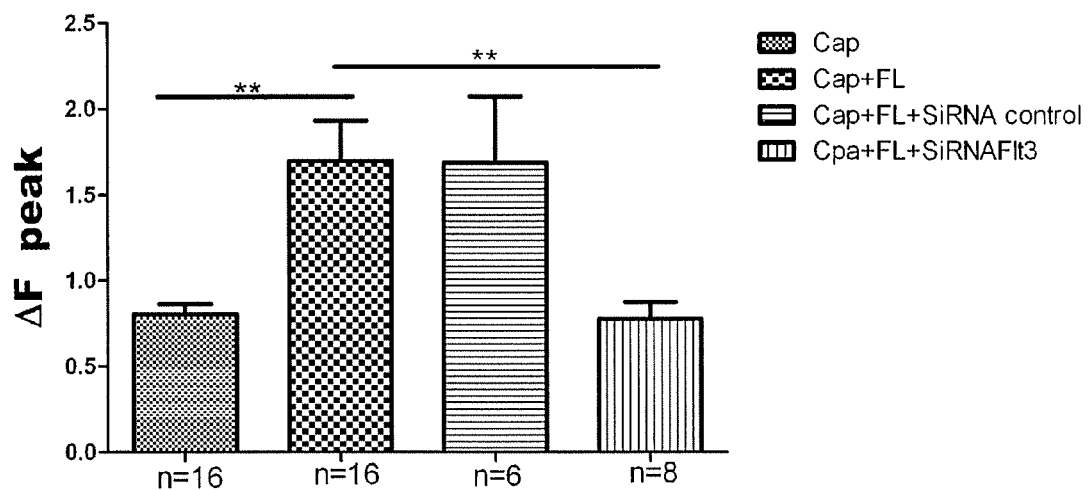
Figure 4B:
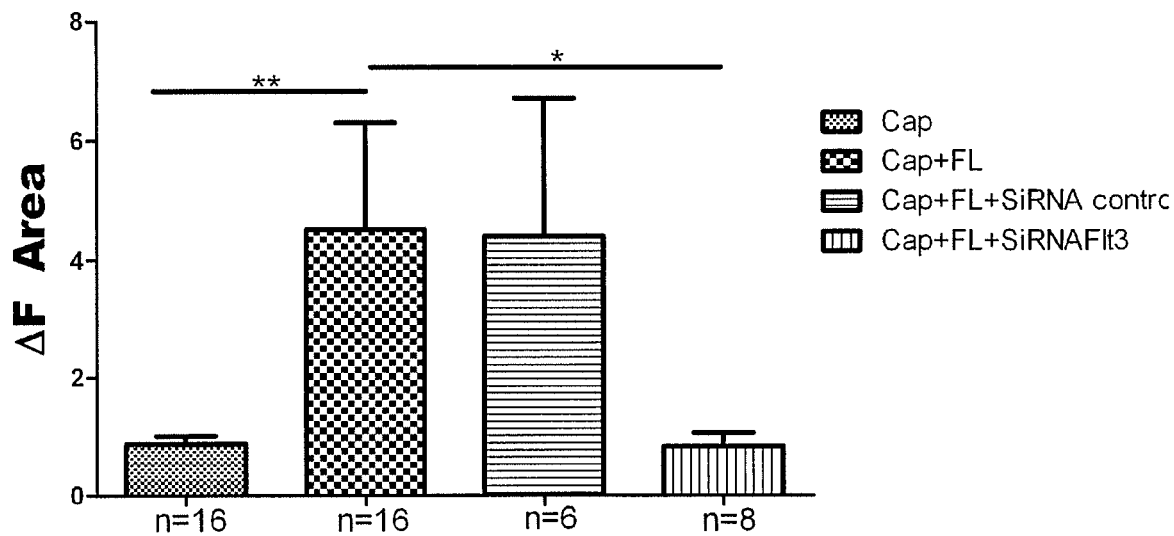

FIG. 4A-B: siRNA against FLT3 inhibits FL-induced potentiation of capsaicin-activated TRPV1 receptors in primary sensory neurons in vitro. (A) ΔFpeak of capsaicin responses in the absence or the presence of FL alone, FL with control siRNA, FL with FLT3 siRNA $P<0.01$. (B) ΔFarea of capsaicin responses in the absence or the presence of FL alone, FL with control siRNA, FL with FLT3 siRNA $P<0.01$.

Figure 5:
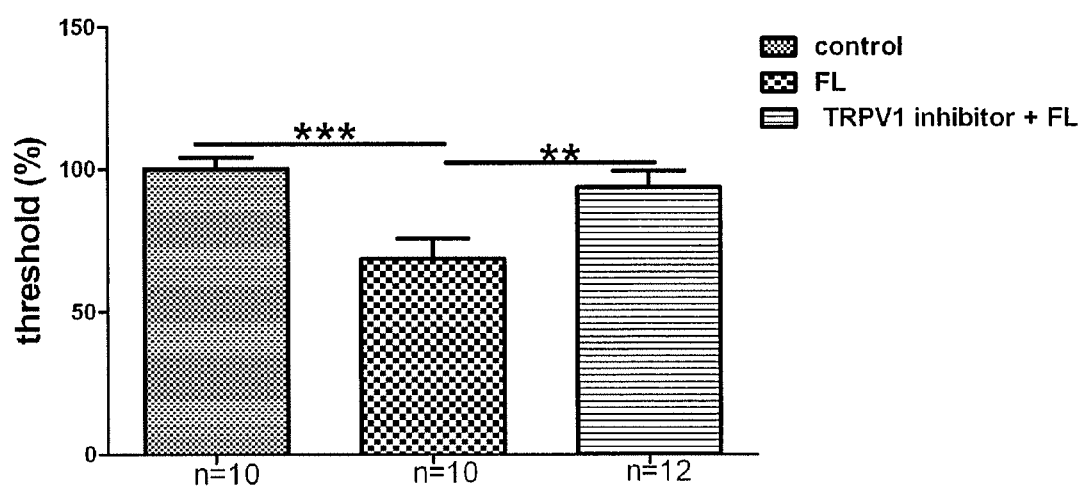

FIG. 5: The TRPV1 inhibitor sb-366791 inhibit FL-induced mechanical hyperalgesia in vivo: Behavioral analysis of the effect of intraplantar-delivered TRPV1 inhibitor sb-366791 (10 μl at 30 μg/ml) on the foot withdrawal response to von Frey hair filaments after FL injection. $P<0.01$; *$P<0.001$.

Figure 6:
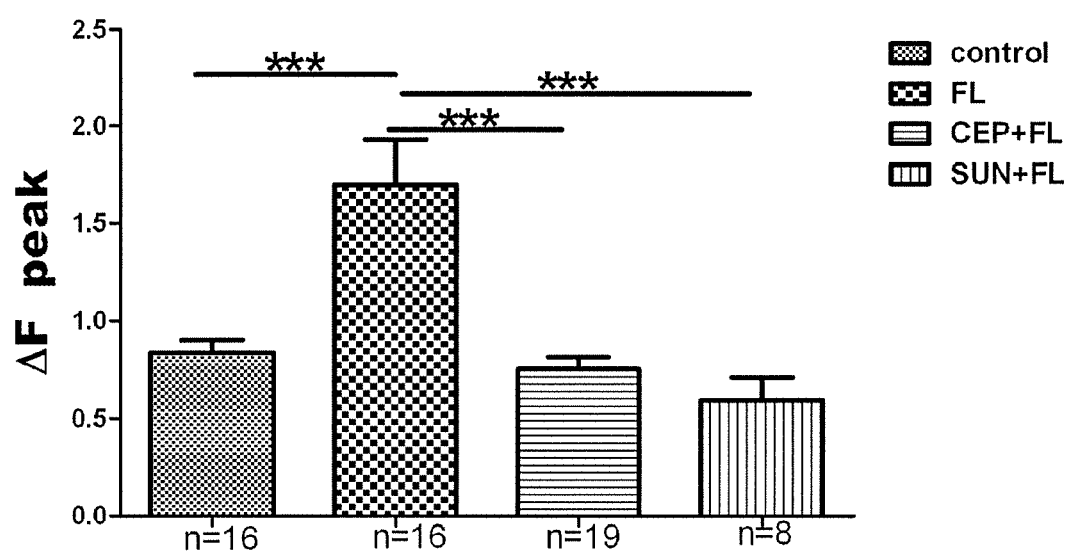

FIG. 6: CEP-701 and SU-11248 inhibits FL-induced potentiation of capsaicin-activated TRPV1 receptors in primary sensory neurons in vitro. ΔFpeak of capsaicin responses in the absence or the presence of FL alone, FL with CEP-701 (CEP; 200 nM), FL with SU-11248 (SUN; 25 nM) ***$P<0.001$.

Figures 7A, 7B:
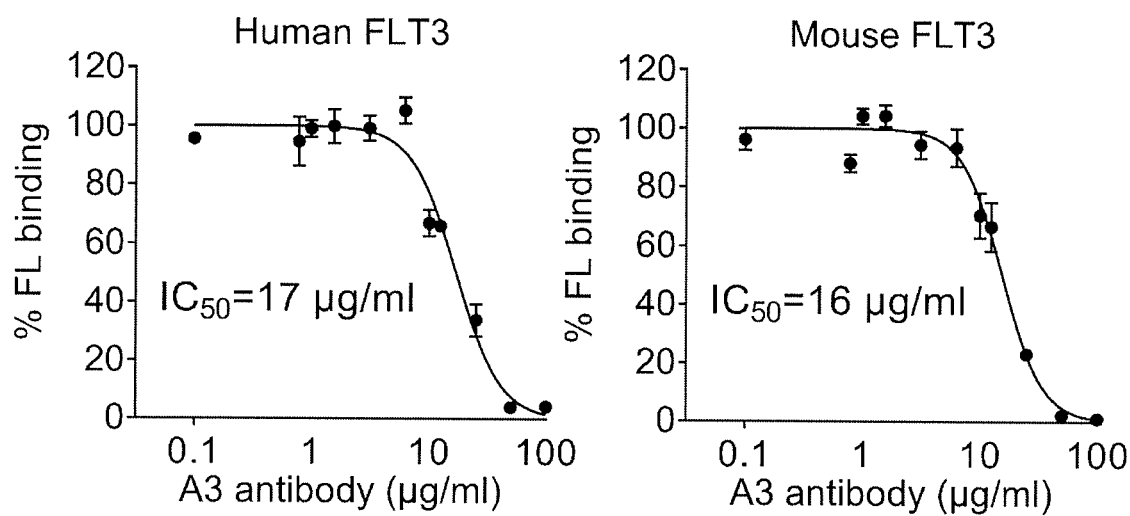

FIG. 7A-B shows that the selected A3 antibody inhibits FL binding to recombinant human and mouse full-length FLT3 expressed in HEK293 cells. A: binding to human FLT3. B: binding to mouse FLT3. Ordinate: FL binding, expressed as percentage of binding.

Figure 8:
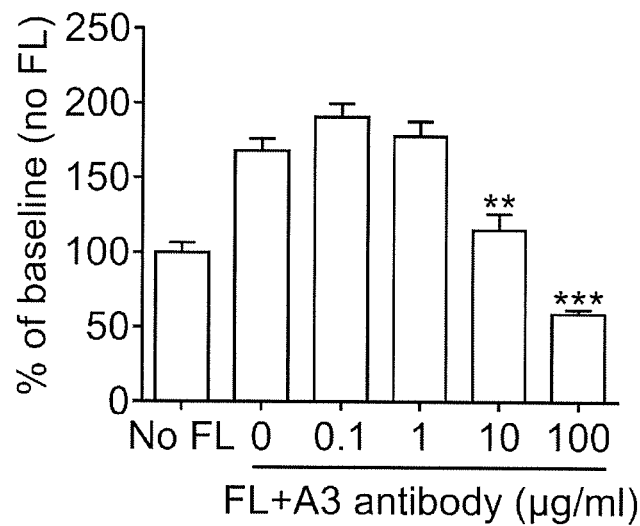

FIG. 8 shows that the selected anti-FLT3 A3 antibody inhibits FL-induced FLT3 autophosphorylation at 10 and 100 μg/ml in RS4-11 cells. *$P<0.05$; **$P<0.1$ vs. FL alone. Abscissa, bars from left to right: (i) No FL; (ii) FL and no A3 antibody; (iii) FL and 0.1 μg/ml A3 antibody; (iv) FL and 1 μg/ml A3 antibody; (v) FL and 10 μg/ml antibody; (vi) FL and 100 μg/ml A3 antibody. Ordinate: FL-induced FLT3 autophosphorylation, as expressed as percent of baseline (reference: no FL).

Figure 9:
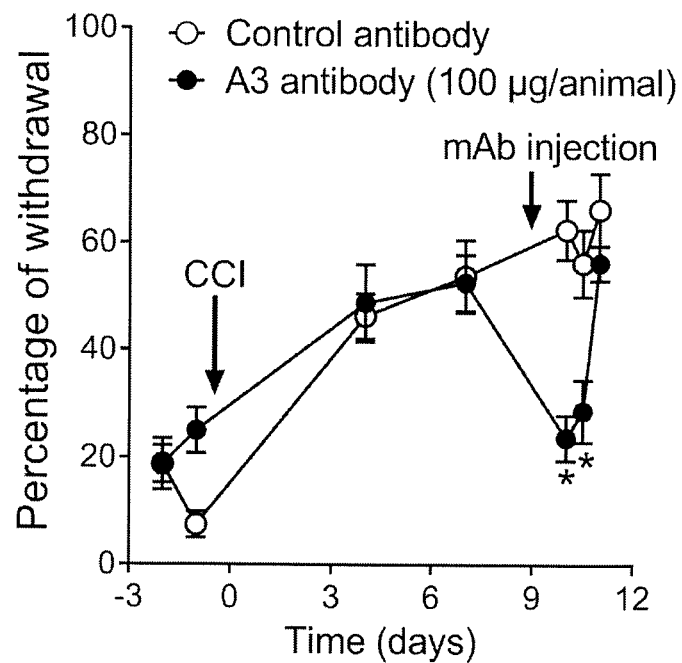

FIG. 9 shows that the selected anti-FLT3 A3 antibody produces a 48 h-lasting inhibition of Chronic-Constriction Injury (CCI)-induced pain hypersensitivity after a single injection at a dose of 100 μg/animal. *$P<0.05$ versus control antibody. Abscissa: Time period before (expressed as negative units) and after (expressed as positive units) Chronic Constriction Injury (see the arrow on the left part of FIG. 9), as expressed in days. Time of antibody injection figured by the arrow on the right part of FIG. 9. Symbol "-○-": Control antibody. Symbol "-●-": A3 antibody. Ordinate: Percentage of withdrawal.

EXAMPLE 1

Material & Methods

Animals: Adult Swiss mice (8-10 week old) (CERJ, Le Genest St Isle, France) were used according to the guidelines of the International Association for the Study of Pain. Mice were housed in cages with a 12/12 hr light/dark cycle and fed food and water ad libitum.

Behavioral experiments: Behavioral responsiveness of the mice was tested following one week of habituation to the testing environment and the observer.

Mechanical withdrawal thresholds: The sensitivity to punctuate mechanical stimuli was assessed using the dynamic plantar aesthesiometer (Bioseb, France). Each mouse was placed in a Plexiglass chamber. Sixty minutes later, a mechanical stimulus (a small-diameter blunt metallic filament) was applied to the plantar surface with an increasing force and the paw withdrawal latencies were measured. For each point, mice were tested three times and the responses for each paw were averaged.

Thermo-nociceptive testing: Nociceptive threshold to acute thermal stimulation was measured using the paw retrieval test (Bioseb, France). Focused light from 12.5 W projection bulb was applied to the middle of the plantar surface of the hind paw (3 mm diameter). The projection bulb was turned off as soon as the mouse removed its paw, and a digital timer connected in series measured the paw withdrawal latency to an accuracy of 0.1 s. We used a cut-off latency of 15 s to avoid the possibility of tissue damage. For each point, mice were tested three times and the responses for each paw were averaged.

Gene Knock-down Experiments:

Small interfering RNAs (siRNAs): Pooled nontargeting control siRNA or specific siRNA against FLT3 (flk2) used in this study were the on-target plus SMART pools from Dharmacon (Perbio Science, Brebières, France; Dharmacon Catalog # L-002000-00-0005 targeting FLT3.

Preparation of the RNA polymer complex: The method used for intrathecal delivery was adapted from one previously reported (Tan et al., 2005). For polyethylenimine (PEI) complex formation, 5 µg specific or nonspecific siRNAs were complexed with 1.8 µl of 200 µM linear low molecular weight PEI ExGen 500 (Euromedex, Souffelweyersheim, France). RNA-polymer complexes were allowed 10 min to form at room temperature. To allow visualization of transfected cells, 3 mM dextran-tetramethylrhodamine (Invitrogen, Cergy Pontoise, France) were added to the 5% glucose solution containing the RNA-polymer complex.

In vivo delivery of siRNA: 6-8 µl of the final solution were injected through the subarachnoid space at the L5-S 1 level of adult mice once a day for 5 days as previously described (Boudes et al, 2009). Animals were allowed 1 days recovery then were either used for behavioural testing or sacrificed and lumbar L4-L5 DRG collected and processed for [Ca2+]i imaging. In preliminary experiments, intrathecal transfection efficiency was evaluated with a GFP siRNA tagged with rhodamine (Qiagen, Courtaboeuf, France) injected in an actin-GFP mice. Fluorescence analysis of rhodamine tagged neurons on DRG slices demonstrated that 50-80% of neurons were transfected with this method and that transfected neurons did not express GFP, evaluated as a lack of co-staining between green GFP and red siRNA.

DRG neurons primary culture: Primary neuronal cultures were established from lumbar (L4 to L6) dorsal root ganglia (DRG) of adult mice as previously described (Boudes et al, 2009). Ganglia were treated twice with collagenase A (1 mg/ml, Roche Diagnostic, France) for 45 minutes (37° C.) and then with trypsin-EDTA (0.25%, Sigma, St Quentin Fallavier, France) for 30 minutes. They were mechanically dissociated by passing 8 to 10 times through the tip of a fire-polished Pasteur pipette in neurobasal (Life Technologies, Cergy Pontoise, France) culture medium supplemented with 10% foetal bovine serum and DNase (50 U/ml, Sigma, St Quentin Fallavier, France). Isolated cells were collected by centrifugation and suspended in neurobasal culture medium supplemented with 2% B27 (Life Technologies), 2 mM glutamine, penicillin/streptomycin (20 U/ml, 0.2 mg/ml). Dissociated neurons were plated on poly-D,L-ornithine (0.5 mg/ml)-laminin (5 µg/ml)-coated glass coverslips at a density of 2500 neurons per well and were incubated in an incubator with a humidified 95% air/5% CO2 atmosphere. Two hours after plating, the culture medium was carefully removed and replaced to eliminate dead cells and tissue debris. The cells were maintained in culture at 37° C. until experiments were performed.

Measurements of intracellular $Ca^{2+}$ ($[Ca^{2+}]_i$): For intracellular $Ca^{2+}$ measurements, DRG neurons were used 18-30 h after plating as described previously. The cells were loaded with a Lock solution containing 2.5 µM Fura2-AM (Molecular probes, Invitrogen, France) by incubation at 37° C. for 30 minutes. The loading solution was washed three times and the Fura2-AM was left to de-esterified for 20 minutes at 37° C. During $[Ca^{2+}]_i$ measurements, perfusion rate of the cells was controlled with a gravity flow system, and the temperature was maintained at 37° C. using an in-line heating system (Warner Instruments). Drugs were delivered with a rapid-switching local perfusion system.

Cells were imaged with a inverted microscope equipped with a NEOFLUAR 25×0.8 objective lens (Axiovert 200, Zeiss, Le Pecq, France) and a CCD camera (Cool SNAP ES, Roper Scientific, France). Lambda DG-4 filter changer (Sutter Instrument, Novato, Calif., USA) was used for switching between 340 nm and 380 nm excitation wavelengths. A Fura filter cube with 400 long pass dichroic and D510/40m emission band pass was used to collect fluorescence emissions separately for each wavelength. Images were acquired and analyzed with Metafluor software (Molecular Devices). Changes in intracellular calcium concentrations ($[Ca^{2+}]_i$) were monitored as changes of the ratio of the fura-2-fluorescence intensity recorded at 340 nm and 380 nm excitation wavelengths ($\Delta F_{340/380}$).

Cells with a robust response to high K+ application (50 mM) at the end of the protocol and a peak response to capsaicin (100 µM)>0.2 $\Delta F_{340/380}$ were retained. $Ca^{2+}$ peak response was easily distinguished from optical noise (<0.02 $\Delta F_{340/380}$). Capsaicin at 100 µM elicited a response >0.2 $\Delta F_{340/380}$ from the maximal number of cells and response magnitudes decreased with subsequent agonist presentation as previously described (Bonnington, J. K., and McNaughton, 2003).

Each neuron was stimulated three times by capsaicin at 4-5 min interval. $Ca^{2+}$ response peak and area data are presented as the ratio of post-FL capsaicin response to the second naïve capsaicin response in individual cells ($\Delta F_{peak}$, $\Delta F_{area}$). Response areas were calculated as a measure of total $Ca^{2+}$ influx. The portion of the calcium response that was used for this measurement included the entire curve from the initiation of the response until the point at which the calcium signal returned to the prestimulus baseline. Typically, this occurred in <120 s.

Unless otherwise stated, all standard chemicals were purchased from Sigma (France) except FL (from ABCYS SA, Paris, France). They were dissolved or conditioned in double distilled water or DMSO or in ethanol according to the recommendations suggested in the Merk Index-13th edition or recommendations from the suppliers. The osmolarity of all the solutions ranged between 298 and 303 mosmol/l.

Statistics: Results are presented as mean ±S.E.M. For comparison between the two groups, the data were analyzed by two-way ANOVA, and if warranted, followed t tests using the computer program Prism (GraphPad, San Diego, Calif.). A p value <0.05 was considered statistically significant.

Results

FL produces thermal and mechanical hyperalgesia in vivo: To investigate the potential role(s) of FL in modulating noxious heat sensitivity in vivo, we first injected FL (100 ng/10 µl) into mice hindpaws, and latency to ipsilateral paw withdrawal from a radiant heat stimulus was measured. We observed a rapid and pronounced heat hyperalgesia within one/two hours which return to control values after 6 day. At 12 H after injection, FL induced a significant thermal hyperalgesia (latency drop around 30%) compared to control mice hindpaws injected with vehicle (p<0.001) (FIG. 1A). For comparison, NGF (100 ng/10 µ) induced a significant latency drop of 25% at 12 H (FIG. 1A).

We next tested the role of FL in modulating noxious mechanical sensitivity in vivo. Injection of FL (100 ng/10 µl) into mice hindpaws resulted in a mechanical hyperalgesia within one/two hours which returned to control values after 6 day. At 12H after injection, FL reduced significantly (p<0.001) the foot withdrawal response to von Frey hair filaments to 50% compared to control mice hindpaws injected with vehicle (FIG. 1B). For comparison, NGF (100ng/10µl) induced a foot withdrawal response decrease of 30% at 12 H (P<0.001) (FIG. 1B).

To test if a specific interaction between FL and its cognate high affinity FLT3 receptor regulates the thermal and mechanical hyperalgesia induced by paw injection of FL, we designed RNA interference experiments to inhibit FLT3 expression (see Materials and Methods). Mice were directly injected into the L4-L5 subarachnoid space during 4 days either with control siRNA (siRNA control group) or siRNA against FLT3 (1 µg/µl of siRNA) (siRNA FLT3 group). After hindpaw injection of FL, siRNA control mice showed thermal and mechanical hyperalgesia to a similar extent as that of non siRNA treated mice at 4 h, 12 h, 1, 2, 3, 5, 7 and 9 days post-injection. In marked contrast, mice that received siRNA against FLT3 did not show hyperalgesia throughout the 9-d test period (FIGS. 2A and 2B for comparison at 12h post-injection; p<0.001).

These data suggest that FL, via its specific interaction with FLT3, plays a critical role in modulating noxious thermal and mechanical pain sensitivity in vivo.

FL potentiates the TRPV1-dependent capsaicin responses in sensory DRG neurons in vitro: Previous results have shown that the capsaicin TRPV1 receptor is necessary for inflammatory thermal hyperalgesia mediated by NGF and that, in vitro, NGF acutely potentiates TRPV1 functioning. The next experiments were designed to test the hypothesis that FL modulates TRPV1 signaling. We used FURA-2-based calcium imaging to quantify the increase in [Ca2+]i that follows capsaicin application to TRPV1 positive sensory neurons. As previously shown, repetitive capsaicin puffs induced TRPV1 channel responses that showed significant tachyphylaxis which reflects a desensitization of the ionotropic receptor (Bonnington, J. K., and McNaughton, 2003). When the cells are exposed to NGF between the applications, a maintained or an increased TRPV1 response magnitude is observed, indicating a sensitization of TRPV1 receptor by NGF (Bonnington, J. K., and McNaughton, 2003). In the present study, potentiated cells were defined as having a response to capsaicin greater in magnitude to the mean of the control response plus two standard deviations. At 10 and 100 ng/ml, FL induced a very robust potentiation of the capsaicin response in 56% of the cells that respond to capsaicin (FIG. 3A). In our standard protocol, FL was concomitantly applied with the third capsaicin application indicating that the effect of FL may be very rapid. The mean fold increase in TRPV1 response (that include all capsaicin responders, both potentiated and unaffected, in the population) was 212% for ΔFpeak and ≈512% for ΔFarea (p<0.001) (FIG. 3B).

Here again, we designed RNA interference experiments to inhibit FLT3 expression in order to test if a specific interaction between FL and its cognate high affinity FLT3 receptor regulated the potentiation of capsaicin-evoked responses in sensory neurons by FL (see Materials and Methods). Capsaicin-responder sensory neurons injected with siRNA control showed a FL-induced sensitization in [Ca2+]i response similar to non-transfected control neurons (FIGS. 4A and B). In marked contrast, neurons that received siRNA against FLT3 did not show any potentiation of the capsaicin response after FL application in comparison to control and control siRNA-treated sensory neurons (p<0.001) (FIGS. 4A and B).

To investigate the potential role(s) of FL in modulating noxious sensitivity through the activation of TRPV1 receptor in vivo, we tested the effect of the TRPV1 inhibitor sb-366791 on the FL-induced mechanical hyperalgesia. At 12 h after injection, FL reduced significantly the foot withdrawal response latency to von Frey hair filaments compared to control mice hindpaws injected with vehicle as described above (FIG. 2A; FIG. 5). In marked contrast, mice that received sb-366791 (intraplantar injection of 10 µl at 30 µg/ml, one hour before FL injection), did not show any change in the foot withdrawal response to von Frey hair filaments in comparison with control mice (FIG. 5).

The present data strongly suggest that FL potentiates in vitro the functioning of the capsaicin-sensitive TRPV1 ionotropic receptor in a subpopulation of nociceptive sensory neurons.

Kinase inhibitors with activity against FLT3 inhibits FL-induced potentiation of capsaicin-activated TRPV1 receptors in primary sensory neurons in vitro: Several small molecules kinase inhibitor with activity against FLT3, both in vitro and in vivo, are already available. Two of them, already used in clinical trials, CEP-701 (lestaurtinib) and sunitinib (SU-11248), were tested for their capacity to inhibit the potentiation of capsaicin-evoked responses in sensory neurons by FL in vitro.

Neurons incubated in the presence of either CEP-701 (200 nM) or sunitinib (25 nM) did not show any sensitization in capsaicin [Ca2+]i response after FL application in contrast to control sensory neurons (p<0.001) (FIG. 6).

Altogether, these finding are consistent with the idea that treatment with FL, through a specific interaction with its high-affinity cognate receptor FLT3, can produce acute thermal and mechanical hyperalgesia in vivo, probably by directly sensitizing TRPV1 receptor in a subpopulation of nociceptors.

EXAMPLE 2

This example describes human monoclonal antibodies against FLT3 receptor used for the treatment of chronic pain disorders.

The antibody A3 against FLT3 exemplified in present example 2 is characterized by one or more functional properties such that this antibodies consists of a human antibody, binds with high affinity to the ECD of human recombinant FLT3, is able to cross-react between the murine and human recombinant forms of FLT3, inhibits the binding of FL to human and mouse recombinant FLT3 (FIG. 7) and is a functional antagonist of human recombinant FLT3 (FIG. 8). The human monoclonal antibody A3 is surprisingly highly potent to antagonize native FLT3 in sensory neurons (FIG. 9) and highly efficacious to inhibit neuropathic pain in a murine model (FIG. 10).

The CDRs of the heavy chain variable domain are located at residues 31-35 (H-CDR1), residues 50-65 (H-CDR2) and residues 95-102 (H-CDR3) according to the Kabat numbering system. The CDRs of the light chain variable domain are located at residues 24-34 (L-CDR1), residues 50-56 (L-CDR2) and residues 89-97 (L-CDR3) according to the Kabat numbering system.

According to the present Example 2, the VH region of the A3 antibody consists of the sequence of SEQ ID NO:1 which is defined as follows and the Kabat numbered sequence is defined in Table A.

SEQ ID NO: 1
EVQLVESGGSLVKPGGSLRLSCAASGFTFSNSYMNWVRQAPGKGLEWISD

ISGSSRDIDYADFVKGRFTISRDNATNSLYLQMNSLRAEDTAVYYCVRSG

NSGMDVWGRGTLVTVSS

TABLE A

Kabat numbered sequence of the VH domain of A3

| Position in SEQ ID NO: 1 | Kabat numbering | Amino acid |
|---|---|---|
| 1 | 1 | E |
| 2 | 2 | V |
| 3 | 3 | Q |
| 4 | 4 | L |
| 5 | 5 | V |
| 6 | 6 | E |
| 7 | 7 | S |
| 8 | 8 | G |
| 9 | 9 | G |
| 10 | 10 | S |
| 11 | 11 | L |
| 12 | 12 | V |
| 13 | 13 | K |
| 14 | 14 | P |
| 15 | 15 | G |
| 16 | 16 | G |
| 17 | 17 | S |
| 18 | 18 | L |
| 19 | 19 | R |
| 20 | 20 | L |
| 21 | 21 | S |
| 22 | 22 | C |
| 23 | 23 | A |
| 24 | 24 | A |
| 25 | 25 | S |
| 26 | 26 | G |
| 27 | 27 | F |
| 28 | 28 | T |
| 29 | 29 | F |
| 30 | 30 | S |
| 31 | 31 | N |
| 32 | 32 | S |
| 33 | 33 | Y |
| 34 | 34 | M |
| 35 | 35 | N |
| 36 | 36 | W |
| 37 | 37 | V |
| 38 | 38 | R |
| 39 | 39 | Q |
| 40 | 40 | A |
| 41 | 41 | P |
| 42 | 42 | G |
| 43 | 43 | K |
| 44 | 44 | G |
| 45 | 45 | L |
| 46 | 46 | E |
| 47 | 47 | W |
| 48 | 48 | I |
| 49 | 49 | S |
| 50 | 50 | D |
| 51 | 51 | I |
| 52 | 52 | S |
| 53 | 52A | G |
| 54 | 53 | S |
| 55 | 54 | S |
| 56 | 55 | R |
| 57 | 56 | D |
| 58 | 57 | I |
| 59 | 58 | D |
| 60 | 59 | Y |
| 61 | 60 | A |
| 62 | 61 | D |
| 63 | 62 | F |
| 64 | 63 | V |
| 65 | 64 | K |
| 66 | 65 | G |
| 67 | 66 | R |
| 68 | 67 | F |
| 69 | 68 | T |
| 70 | 69 | I |
| 71 | 70 | S |
| 72 | 71 | R |
| 73 | 72 | D |
| 74 | 73 | N |
| 75 | 74 | A |
| 76 | 75 | T |
| 77 | 76 | N |
| 78 | 77 | S |
| 79 | 78 | L |
| 80 | 79 | Y |
| 81 | 80 | L |
| 82 | 81 | Q |
| 83 | 82 | M |
| 84 | 82A | N |
| 85 | 82B | S |
| 86 | 82C | L |
| 87 | 83 | R |
| 88 | 84 | A |
| 89 | 85 | E |
| 90 | 86 | D |
| 91 | 87 | T |
| 92 | 88 | A |
| 93 | 89 | V |
| 94 | 90 | Y |
| 95 | 91 | Y |
| 96 | 92 | C |
| 97 | 93 | V |
| 98 | 94 | R |
| 99 | 95 | S |
| 100 | 96 | G |
| 101 | 97 | N |
| 102 | 98 | S |
| 103 | 99 | G |
| 104 | 100 | M |
| 105 | 101 | D |
| 106 | 102 | V |
| 107 | 103 | W |
| 108 | 104 | G |
| 109 | 105 | R |
| 110 | 106 | G |
| 111 | 107 | T |
| 112 | 108 | L |
| 113 | 109 | V |
| 114 | 110 | T |
| 115 | 111 | V |
| 116 | 112 | S |
| 117 | 113 | S |

Accordingly, the H-CDR1 of A3 is defined by the sequence ranging from the amino acid residue at position 31 to the amino acid residue at position 35 in SEQ ID NO:1. The H-CDR1 of A3 is thus the amino acid sequence NSYMN (SEQ ID NO: 3).

Accordingly, the H-CDR2 of A3 is defined by the sequence ranging from the amino acid residue at position 50 to the amino acid residue at position 66 in SEQ ID NO: 1. The H-CDR2 of A3 is thus the amino acid sequence DISGSSRDIDYADFVKG (SEQ ID NO: 4).

Accordingly, the H-CDR3 of A3 is defined by the sequence ranging from the amino acid residue at position 99 to the amino acid residue at position 106 in SEQ ID NO: 1. The H-CDR3 of A3 is thus the amino acid sequence SGNSGMDV (SEQ ID NO: 5).

According to the present example 2, the VL region of the A3 antibody consists of the sequence of SEQ ID NO:2 which is defined as follows and the Kabat numbered sequence is defined in Table B.

SEQ ID NO: 2:
QSVLTQPASVSGSPGQSITISCAGTSSDVGGGYYVSWYQQHPGKAPKLMI

YYDSYRPSGVSNRFSGSKSGNTASLTISGLQAEDEADYYCSSYTNNSTRV

FGGGTKLEIK

TABLE B

Kabat numbered sequence of the VL domain of A3

| Position in SEQ ID NO: 2 | Kabat numbering | Amino acid |
|---|---|---|
| 1 | 1 | Q |
| 2 | 2 | S |
| 3 | 3 | V |
| 4 | 4 | L |
| 5 | 5 | T |
| 6 | 6 | Q |
| 7 | 7 | P |
| 8 | 8 | A |
| 9 | 9 | S |
| 10 | 10 | — |
| 11 | 11 | V |
| 12 | 12 | S |
| 13 | 13 | G |
| 14 | 14 | S |
| 15 | 15 | P |
| 16 | 16 | G |
| 17 | 17 | Q |
| 18 | 18 | S |
| 19 | 19 | I |
| 20 | 20 | T |
| 21 | 21 | I |
| 22 | 22 | S |
| 23 | 23 | C |
| 24 | 24 | A |
| 25 | 25 | G |
| 26 | 26 | T |
| 27 | 27 | S |
| 28 | 27A | S |
| 29 | 27B | D |
| 30 | 27C | V |
| 31 | 28 | G |
| 32 | 29 | G |
| 33 | 30 | G |
| 34 | 31 | Y |
| 35 | 32 | Y |
| 36 | 33 | V |
| 37 | 34 | S |
| 38 | 35 | W |
| 39 | 36 | Y |
| 40 | 37 | Q |
| 41 | 38 | Q |
| 42 | 39 | H |
| 43 | 40 | P |
| 44 | 41 | G |
| 45 | 42 | K |
| 46 | 43 | A |
| 47 | 44 | P |
| 48 | 45 | K |
| 49 | 46 | L |
| 50 | 47 | M |
| 51 | 48 | I |
| 52 | 49 | Y |
| 53 | 50 | Y |
| 54 | 51 | D |
| 55 | 52 | S |
| 56 | 53 | Y |
| 57 | 54 | R |
| 58 | 55 | P |
| 59 | 56 | S |
| 60 | 57 | G |
| 61 | 58 | V |
| 62 | 59 | S |
| 63 | 60 | N |
| 64 | 61 | R |
| 65 | 62 | F |
| 66 | 63 | S |
| 67 | 64 | G |
| 68 | 65 | S |
| 69 | 66 | K |
| 70 | 67 | S |
| 71 | 68 | G |
| 72 | 69 | N |
| 73 | 70 | T |
| 74 | 71 | A |
| 75 | 72 | S |
| 76 | 73 | L |
| 77 | 74 | T |
| 78 | 75 | I |
| 79 | 76 | S |
| 80 | 77 | G |
| 81 | 78 | L |
| 82 | 79 | Q |
| 83 | 80 | A |
| 84 | 81 | E |
| 85 | 82 | D |
| 86 | 83 | E |
| 87 | 84 | A |
| 88 | 85 | D |
| 89 | 86 | Y |
| 90 | 87 | Y |
| 91 | 88 | C |
| 92 | 89 | S |
| 93 | 90 | S |
| 94 | 91 | Y |
| 95 | 92 | T |
| 96 | 93 | N |
| 97 | 94 | N |
| 98 | 95 | S |
| 99 | 95A | T |
| 100 | 96 | R |
| 101 | 97 | V |
| 102 | 98 | F |
| 103 | 99 | G |
| 104 | 100 | G |
| 105 | 101 | G |
| 106 | 102 | T |
| 107 | 103 | K |
| 108 | 104 | L |
| 109 | 105 | E |
| 110 | 106 | I |
| 111 | 106A | K |

Accordingly, the L-CDR1 of A3 is defined by the sequence ranging from the amino acid residue at position 24 to the amino acid residue at position 37 in SEQ ID NO:2. The L-CDR1 of A3 is thus the amino acid sequence AGTSSDVGGGYYVS (SEQ ID NO: 6).

Accordingly, the L-CDR2 of A3 is defined by the sequence ranging from the amino acid residue at position 53 to the amino acid residue at position 59 in SEQ ID NO:2. The L-CDR2 of A3 is thus the amino acid sequence YDSYRPS (SEQ ID NO: 7).

Accordingly, the L-CDR3 of A3 is defined by the sequence ranging from the amino acid residue at position 92 to the amino acid residue at position 101 in SEQ ID NO:2. The L-CDR3 of A3 is thus the amino acid sequence SSYTNNSTRV (SEQ ID NO: 8).

Accordingly, the present example 2 relates to a human monoclonal antibody against FLT3 comprising a heavy chain comprising i) a H-CDR1 having at least 50% of identity with the H-CDR1 of A3, ii) a H-CDR2 having at least 50% of identity with the H-CDR2 of A3 and iii) a H-CDR3 having at least 50% of identity with the H-CDR3 of A3 or a light chain comprising i) a L-CDR1 having at least 50% of identity with the L-CDR1 of A3, ii) a L-CDR2 having at least 50% of identity with the L-CDR2 of A3 and iii) a L-CDR3 having at least 50% of identity with the L-CDR3 of A3 wherein:
the H-CDR1 of A3 is defined by the sequence ranging from the amino acid residue at position 31 to the amino acid residue at position 35 in SEQ ID NO:1,
the H-CDR2 of A3 is defined by the sequence ranging from the amino acid residue at position 50 to the amino acid residue at position 66 in SEQ ID NO:1, the H-CDR3 of A3 is defined by the sequence ranging from the amino acid residue at position 99 to the amino acid residue at position 106 in SEQ ID NO:1, the L-CDR1 of A3 is defined by the sequence ranging from the amino acid residue at position 24 to the amino acid residue at position 37 in SEQ ID NO:2, the L-CDR2 of A3 is defined by the sequence ranging from the amino acid residue at position 53 to the amino acid residue at position 59 in SEQ ID NO:2, and, the L-CDR3 of A3 is defined by the sequence ranging from the amino acid residue at position 92 to the amino acid residue at position 101 in SEQ ID NO:2.

In an embodiment, the human monoclonal antibody of example 2 comprises a heavy chain having i) the H-CDR1 of A3, ii) the H-CDR2 of A3 and iii) the FI-CDR3 of A3.

In an embodiment, the human monoclonal antibody of the invention comprises a light chain having i) the L-CDR1 of A3, ii) the L-CDR2 of A3 and iii) the L-CDR3 of A3.

In a particular embodiment, the human monoclonal antibody according to example 2 comprises a heavy chain having i) the H-CDR1 of A3, ii) the H-CDR2 of A3 and iii) the H-CDR3 of A3 and a light chain having i) the L-CDR1 of A3, ii) the L-CDR2 of A3 and iii) the L-CDR3 of A3.

The A3 antibody was expressed as a fully human IgG1 molecule with a Fc deficient in ADCC and CDC activities.

The human monoclonal antibodies of the present example 2 may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

EXAMPLE 2 is illustrated by the following Additional Figures. These Figures should not be interpreted in any way as limiting the scope of the present invention.

Obtention of the A3 Antibody

The A3 antibody directed against FLT3 was produced by a phage display strategy and the antibody selection was performed by using ECD of human or mouse recombinant FLT3 produced in NSO cell line. To identify antibodies cross-reacting with both human and mouse FLT3, phages were selected by three rounds of panning, according to methods well known in the art (Philibert, P. et al. A focused antibody library for selecting scFvs expressed at high levels in the cytoplasm. BMC Biotechnol. 7, 81; 2007), first against the ECD of human FLT3, then against the ECD of mouse FLT3 and then against the ECD of human FLT3. A batch of one selected antibody named A3 was tested for its ability to bind to the ECD of human or mouse recombinant FLT3 using an ELISA technique. For this, recombinant proteins were coated in a 96-well microtiter plate, the purified A3 antibody was added at a concentration of 10 µg/mL, and bound- antibodies revealed using an anti-human antibody conjugated to Horse Radish Peroxidase enzyme and 3,3',5,5'-tétraméthylbenzidine as a substrate. The A3 antibody generates immunoreactivity against Fc fragments coupled to EDC of human or mouse FLT3 (Fc-ECDhFLT3 or Fc-ECDmFLT3), but not against the Fc fragment alone.

The Antibody A3 Inhibits FL Binding to Mouse and Human FLT3

The binding of the A3 antibody to full-length hFLT3 and mFLT3 was measured by displacement of extracellular FL binding on recombinant HEK cells by using time-resolved fluorescence resonance energy transfer (TR-FRET).

Methods:

Chemicals and reagents. The Tag-lite® labeling medium was from Cisbio Bioassays (Condolet, France). The Lumi4-Tb derivative of O6-Benzylguanine was synthesized by Cisbio Bioassays and is commercialized as SNAP-Lumi4-Tb (Cisbio Bioassays, Ref. SSNPTBE).

A recombinant rh-FLT3-L was produced as previously reported (Verstraete K, et al. Efficient production of bioactive recombinant human Flt3 ligand in *E. coli*. Protein J, 2009 28: 57-65) and labeled with a red fluorescent probe (Red-FL). Poly-L-ornithine (MW of 30,000-70,000 daltons) was from Sigma-Aldrich. The plasmids encoding for the SNAP tagged human FLT3 (pSNAP-hFLT3) or the mouse FLT3 (pSNAP-mFLT3) used for transient transfection was obtained from Cisbio Bioassays. Monoclonal antibodies against FLT3 (8F2) and phosphotyrosine FLT3 (PY969) were purchased from Cell Signaling Technology and labeled with Lumi4-Tb and d2 respectively, by Cisbio.

Cell culture. HEK293T cells, used for binding assays, were maintained in DMEM Glutamax (Invitrogen) supplemented with antibiotics (penicillin 50 U/ml, streptomycin 50 µg/ml) and 10% heat-inactivated Fetal Calf Serum.

Transfection procedures. Transfections were performed in 96 well plates pre-coated with Poly-L-Ornithine (50 µof 10 mg/ml), using cell density of 50,000 cells per well. Transfection mixes were prepared using 100 ng of pSNAP-hFLT3 or pSNA-mFLT3 plasmid, 0.25 µl of Lipofectamine® 2000 (Invitrogen) and 50 µOpti-MEM per well. Prior to their addition in plates, transfection mixes were preincubated for 20 min at room temperature. Then 100 µl of HEK293T cells at a density of 500,000 cells/ml were plated in each well and were incubated at 37° C. under 5% CO) for 24 h.

Transient transfections were performed in batches to further generate frozen cells. HEK293T cells in complete cell medium were grown in a T75 cm2 flask placed at 37° C. under 5% CO2. When reaching 80% confluency, the cell medium was removed and replaced by 6 ml of fresh cell culture medium. Then, a transfection mix containing 10 µg plasmid, 25 µl Lipofectamine® 2000 and 4 ml Opti-MEM final volume was incubated for 20 min at room temperature prior to addition on cells. After the addition of mix, the culture flask was incubated at 37° C. under 5% $CO_2$ for 24 h.

Covalent labeling of cells expressing the SNAP tagged-FLT3. Cell culture medium was removed from the 96 well plates and 100 nM of SNAP-Lumi4 Tb, previously diluted in the Tag-lite® labelling medium, was added under 100 µl per well, and further incubated 1 h at 37° C. under 5% CO2. The excess of SNAP-Lumi4-Tb was removed by washing each well 4 times with 100 µl of Tag-lite® labelling medium.

After removal of the cell culture medium from a flask containing adherent cells, 5 ml of Tag-lite® labelling medium containing 100 nM of SNAP-Lumi4-Tb was added to the flask and incubated for 1 h at 37° C. under 5% CO2. The excess of SNAP-Lumi4-Tb was removed by washing each flask 4 times with 5 ml of Tag-lite® labelling medium. Cells were detached, pelleted by centrifugation (5 min at 1,300 rpm) and suspended in a cell culture medium containing 10% DMSO. Then, cells were distributed at 5 million cells per vial and slowly frozen to −80° C. in isopropanol then transferred in liquid nitrogen for storage. Prior to their use, the frozen cells were thawed quickly at 37° C., the medium was removed from the vials and the cells were suspended in the Tag-lite® labelling medium at a cell-density of 1 million cells/ml.

TR-FRET binding assays. TR-FRET binding assays were performed 24 h after transfection on fresh cells. When using frozen cells, binding assays were carried out immediately after cells thawing. When the assay was carried out on adherent cells in 96-well plates, the cell density was 50,000 cells per well, while a density of 10,000 cells per well was used to carry out binding assays in suspension in 384-well small volume plates.

Cells were incubated with 0.5 nM Red-FL in the presence of increasing concentrations of the antibody. In the plates containing labelled cells, 50 µl of Tag-lite® labelling medium, 25 µl of compounds to be tested were added and incubated for 1 h at room temperature prior to the addition of 25 µl of Red-FL. Plates were then incubated at room temperature for 4 h or overnight before signal detection.

Signal detection. Signal was detected using an advanced fluorescence microplate reader (RUBYstar, BMG Labtech) equipped with a HTRF optic module allowing a donor excitation at 337 nm and a signal collection both at 665 nm and 620 nm. A frequency of 20 flashes/well is selected for the laser excitation. The signal was collected both at 665 nm and 620 nm using the following time-resolved settings: delay 50 µs, integration time 400 µs. HTRF ratios were obtained by dividing the acceptor signal (665 nm) by the donor signal (620 nm). Results were expressed as percentage of signal measured in the presence of Red-FL alone, corrected for non-specific binding measured in the presence of 0.5 µM.

Results:

As shown in FIG. 7, the A3 antibody displaces FL binding to HEK cells expressing full-length hFLT3 (FIG. 7A) or mFLT3 (FIG. 7B) with $IC_{50}$ of about 17 µg/ml.

The A3 Antibody Antagonizes FL-Induced FLT3 Activation in RS4-11 Cells

Methods

Cell. RS4-11 cells, used for auto-phosphorylation assays, were maintained in RPMI-1640 (Invitrogen) and 10% Fetal Calf Serum. They were transfected as in the case of HEK cells (see above)

Auto-Phosphorylation assays. A density of 50,000 cells per well was used to carry out this assay in suspension in 384-well small volume plates to determine the degree of phosphorylation of FLT3. In the aim to discover antagonist compounds and to develop this assay, we were determined the efficiency of FL on RS4-11 cells.

Cells were incubated with 1 nM of rh-FL in the presence of increasing concentrations of the antibody. In the plates containing RS4-11 cells (5 µL/well), 5 µL of compounds to be tested were added and incubated for 1 h at room temperature prior to the addition of 2 µof rh-FL at 0.1 µM. After incubation of 3 min at room temperature of rh-FL, 4 µl of lysis buffer were added and incubated for 2 h at room temperature. A mix of anti-FLT3 and an anti-TYR-969 FLT3 antibodies labeled with Lumi4-Tb and d2 respectively (4 µL) diluted in Tag-lites) labelling medium, were added on cell lysate. Plates were then incubated at room temperature for 2 h or overnight before signal detection (as above).

Results

As shown in FIG. 8, the A3 antibody inhibits FL-induced FLT3 autophosphorylation at concentrations of 10 and 100 µg/ml. The A3 antibody is therefore an FLT3 antagonist.

The A3 antibody reverses neuropathic pain in an animal model

The efficacy of the antibody A3 to reverse neuropathic pain was assessed in the Chronic Constriction Injury (CCI) mouse model of persistent peripheral neuropathic pain, consisting in three chronic ligatures tied loosely around the sciatic nerve (Bennett, G. J. & Xie, Y. K. A peripheral mononeuropathy in rat that produces disorders of pain sensation like those seen in man. Pain, 1988, 33:87-107). Neuropathic pain symptoms, such as mechanical hypersensitivity, develop within 10 days post-injury.

Methods:

CCI model. The Chronic Constriction Injury (CCI) model was adapted for mice (Costa, B., Comelli, F., Bettoni, I., Colleoni, M. & Giagnoni, G. The endogenous fatty acid amide, palmitoylethanolamide, has anti-allodynic and anti-hyperalgesic effects in a murine model of neuropathic pain: involvement of CB(1), TRPV1 and PPARgamma receptors and neurotrophic factors. Pain, 2008, 139:541-550). Briefly, skin was incised and the sciatic nerve was exposed unilaterally at the mild-high level by dissecting through the biceps femoris. Three ligations (catgut 6.0) were loosely tied around the sciatic nerve with about 1 mm spacing to reduce blood flow. The skin was then closed with staples.

Mechanical nociception assay. A 0.6 g-von Frey filament was used for hindpaw mechanical hypersensitivity. Sharp withdrawal of the stimulated hindpaw was considered as a positive response. The procedure was applied 10 times and the percentage of positive responses was calculated.

Data and statistical analyses. Data are expressed as the mean ±S.E.M. Statistical significance was determined by two-way analysis of variance (ANOVA) for repeated measures, over time. In all experiments in which a significant result was obtained, the F test was followed by Dunnett's post-hoc test to compare with the control group.

Results:

FIG. 9 describes mechanical hypersensitivity that develops after the CCI injury, which is shown by the increased percentage of withdrawal from a mechanical stimulation of the paw. When mechanical hypersensitivity is maximal, e.g. 9 days after CCI injury, the injection by intraperitoneal route of the A3 antibody, at the dose of 100 µg/animal, completely reduce mechanical sensitivity to the scores obtained before CCI injury, as compared to a control, irrelevant antibody. These results show that the A3 antibody is able to treat neuropathic pain.

REFERENCES

Throughout this application, various references describe the state of the art to which this invention pertains. The disclosures of these references are hereby incorporated by reference into the present disclosure.

Bennett, G J & Xie, Y K. A peripheral mononeuropathy in rat that produces disorders of pain sensation like those seen in man. Pain 33, 87-107 (1988).

Bonnington, J. K., and McNaughton, P. A. (2003). Signalling pathways involved in the sensitisation of mouse nociceptive neurones by nerve growth factor. J. Physiol. 551, 433-446.

Boudes, M, Sar, C, Menigoz, A, Hilaire, C, Pequignot, M, Kozlenkov, V, Marmorstein, A, Carroll, P, Valmier, J, Scamps, F (2009). Best 1/is a gene regulated by nerve injury and required for $Ca^{2+}$-activated current expression in sensory neurons in mice. J. Neurosci. 29, 46, 10060-68

Caterina, M. J., Leffler, A., Malmberg, A. B., Martin, W. J., Trafton, J., Petersen-Zeitz, K. R., Koltzenburg, M., Basbaum, A. I., and Julius, D.; Impaired nociception and pain sensation in mice lacking the capsaicin receptor; Science 2000 288, 306-313.

Chuang, H. H., Prescott, E. D., Kong, H., Shields, S., Jordt, S. E., Basbaum, A. I., Chao, M. V., and Julius, D.; Bradykinin and nerve growth factor release the capsaicin receptor from PtdIns(4,5)P2-mediated inhibition; Nature 2001 411, 957-962.

Davis, J. B., Gray, J., Gunthorpe, M. J., Hatcher, J. P., Davey, P. T., Overend, P., Harries, M. H., Latcham, J., Clapham, C., Atkinson, K.; Vanilloid receptor-1 is essential for inflammatory thermal hyperalgesia; Nature 2000 405, 183-187.

Fabian M A, Biggs W H 3rd, Treiber D K, et al. A small molecule-kinase interaction map for clinical kinase inhibitors. Nat Biotechnol. 2005; 23(3):329-336.

Jordt, S. E., McKemy, D. D., and Julius, D.; Lessons from peppers and peppermint: the molecular logic of thermosensation; Curr Opin Neurobiol 200313, 487-492.

Karaman M W, Herrgard S, Treiber D K, et al. A quantitative analysis of kinase inhibitor selectivity. Nat Biotechnol. 2008; 26(1):127-132.

Li Y, Li H, Wang M N, Lu D, Bassi R, Wu Y, Zhang H, Balderes P, Ludwig D L, Pytowski B, Kussie P, Piloto O, Small D, Bohlen P, Witte L, Zhu Z, Hicklin D J. Suppression of leukemia expressing wild-type or ITD-mutant FLT3 receptor by a fully human anti-FLT3 neutralizing antibody; Blood. 2004 Aug. 15; 104(4):1137-44.

Malin, S. A., Molliver, D. C., Koerber, H. R., Cornuet, P., Frye, R., Albers, K. M., and Davis, B. M.; Glial cell line-derived neurotrophic factor family members sensitize nociceptors in vitro and produce thermal hyperalgesia in vivo; J Neurosci 2006 26, 8588-8599.

Sternberg D W, Licht J D; Therapeutic intervention in leukemias that express the activated fms-like tyrosine kinase 3 (FLT3): opportunities and challenges; Curr Opin Hematol. 2005 Jan;12(1): 7-13.

Verstraete K, Koch S, Ertugrul S, Vandenberghe I, Aerts M, Vandriessche G, Thiede C, Savvides SN. Efficient production of bioactive recombinant human Flt3 ligand in *E. coli*. Protein J 28, 57-65 (2009).

Zarrinkar P, Gunawardane R N, Cramer M D, Gardner M F, Brigham D, Belli B, Karaman M W, Pratz K W, Pallares G, Chao Q, Sprankle K G, Patel H K, Levis M, Armstrong R C, James J, Bhagwat S S; AC220 is a uniquely potent and selective inhibitor of FLT3 for the treatment of acute myeloid leukemia (AML); Blood. 2009 Oct. 1; 114(14): 2984-92.

Verstraete K, et al. Efficient production of bioactive recombinant human Flt3 ligand in *E. coli*. Protein J 28, 57-65 (2009).

The invention claimed is:

1. A method of treating pain disorders in a patient in need thereof, comprising the step of administering to said patient a human monoclonal antibody against FLT3 wherein the human monoclonal antibody comprises a heavy chain having i) the H-CDR1 of A3 (SEQ ID NO: 3), ii) the H-CDR2 of A3 (SEQ ID NO: 4) and iii) the H-CDR3 of A3 (SEQ ID NO: 5) and a light chain having i) the L-CDR1 of A3(SEQ ID NO: 6), ii) the L-CDR2 of A3 (SEQ ID NO: 7) and iii) the L-CDR3 of A3 (SEQ ID NO: 8).

2. The method of claim 1, wherein said pain disorders are selected from the group consisting of acute pain, chronic pain, neuropathic pain, inflammatory pain, low back pain, post-operative pain, cancer pain, and migraine.

* * * * *